(12) United States Patent
Khanna et al.

(10) Patent No.: US 7,867,496 B2
(45) Date of Patent: Jan. 11, 2011

(54) USE OF TGF-β ANTAGONISTS TO LIMIT NEPHROTOXICITY OF IMMUNOSUPPRESSIVE AGENTS

(75) Inventors: Ashwani K. Khanna, Clarksville, MD (US); Steven Ledbetter, Westborough, MA (US)

(73) Assignees: Genzyme Corporation, Cambridge, MA (US); The MCW Research Foundation, Inc., Milwaukee, WI (US); National Institutes of Health, Bethesda, MD (US)

( * ) Notice: Subject to any disclaimer, the term of this patent is extended or adjusted under 35 U.S.C. 154(b) by 325 days.

(21) Appl. No.: 11/663,519

(22) PCT Filed: Sep. 22, 2005

(86) PCT No.: PCT/US2005/033942

§ 371 (c)(1),
(2), (4) Date: Jun. 20, 2008

(87) PCT Pub. No.: WO2006/036729

PCT Pub. Date: Apr. 6, 2006

(65) Prior Publication Data

US 2009/0035304 A1 Feb. 5, 2009

Related U.S. Application Data

(60) Provisional application No. 60/612,187, filed on Sep. 22, 2004.

(51) Int. Cl.
*A61K 39/395* (2006.01)
*A61K 38/13* (2006.01)
*C07K 16/22* (2006.01)
*C07K 11/02* (2006.01)

(52) U.S. Cl. ............ 424/145.1; 424/133.1; 424/141.1; 424/142.1; 424/158.1; 530/317; 530/350; 530/387.3; 530/388.1; 530/388.15; 530/388.24; 530/389.1; 530/389.2; 514/21.1

(58) Field of Classification Search ........................ None
See application file for complete search history.

(56) References Cited

U.S. PATENT DOCUMENTS 6,492,497 B1 12/2002 Thompson et al.
2003/0069248 A1 4/2003 Chakravarty et al.

FOREIGN PATENT DOCUMENTS

WO WO 2004/060362 7/2004

OTHER PUBLICATIONS

International Search Report and Written Opinion for PCT/US2005/033942, mailed May 30, 2006 from the International Searching Authority of the European Patent Office.
Islam et al., "Effect of Anti-Transforming Growth Factor-β Antibodies in Cyclosporine-Induced Renal Dysfunction," Kidney International, 59:498-506, (2001).
Khanna et al., "Anti-Transforming Growth Factor Antibody at Low but Not High Doses Limits Cyclosporine-Mediated Nephrotoxicity Without Altering Rat Cardiac Allograft Survival," Circulation, 110:3822-3829 (2004).
Khanna et al., "Transforming Growth Factor (TGF)-β Mimics and Anti-TGF-β Antibody Abrogates the In Vivo Effects of Cyclosporine: Demonstration of a Direct Role of TGF-β in Immunosuppression and Nephrotoxicity of Cyclosporine," Transplantation, 67:882-889 (1999).
Ling et al., "Therapeutic Role of TGF-β-Neutralizing Antibody in Mouse Cyclosporine A Nephropathy: Morphologic Improvement Associated with Functional Preservation," J. Am. Soc. Nephrol., 14:377-388 (2003).
Ninova et al. "Acute Nephrotoxicity of Tacrolimus and Sirolimus in Renal Isografts: Differential Intragraft Expression of Transforming Growth Factor-β1 and α-Smooth Muscle Actin," Transplantation, 78:338-344 (2004).
Shihab et al., "Sirolimus Increases Transforming Growth Factor-β1 Expression and Potentiates Chronic Cyclosporine Nephrotoxicity," Kidney International, 65:1262-1271 (2004).
Xin et al., "Suppression of Cyclosporine A Nephrotoxicity In Vivo by Transforming Growth Factor β Receptor-Immunoglobulin G Chimeric Protein," Transplantation, 77:1433-1442 (2004).

*Primary Examiner*—David S Romeo
(74) *Attorney, Agent, or Firm*—Finnegan, Henderson, Farabow, Garrett & Dunner, LLP

(57) ABSTRACT

The disclosure relates to methods of ameliorating nephrotoxic side effects of immunosuppressive agents whose immunosuppressive activity is mediated via upregulation of TGF-β such as, for example, cyclosporine (CsA). The disclosure provides treatment modalities for use in patients that require immunosuppression, e.g., patients at risk of transplant rejection or having an autoimmune disease. In the methods of the invention, a TGF-β antagonist, e.g., an anti-TGF-β antibody, is administered to a patient treated with an immunosuppressive agent. Such a TGF-β antagonist is administered in a therapeutically effective amount sufficient to alleviate the nephrotoxic effects of the immunosuppressive agent without substantially interfering with immunosuppressive activity of the agent.

19 Claims, 9 Drawing Sheets

USE OF TGF-β ANTAGONISTS TO LIMIT NEPHROTOXICITY OF IMMUNOSUPPRESSIVE AGENTS

This application claims priority to U.S. provisional application No. 60/612,187, filed on Sep. 22, 2004, which is incorporated by reference herein in its entirety.

TECHNICAL FIELD

The technical field of the invention relates to the fields of organ transplantation (transplantology), clinical immunology, and nephrology. The invention relates to methods of reducing nephrotoxic side effects of certain immunosuppressive agents, including cyclosporine.

BACKGROUND OF THE INVENTION

Immunosuppression is routinely used to reduce the risk of rejection in tissue/organ transplantation as well as a therapy for autoimmune and inflammatory disorders, Cyclosporine A (CsA) is currently the most widely used immunosuppressive agent. Tacrolimus (TAC) (also known as FK506) and sirolumus (also known as rapamycin) are two other commonly used immunosuppressants. For review of various immunosuppressive therapies, see, e.g., Schuurman et al. (2001) Modern Immunosuppressives (Milestones in Drug Therapy), Birkhauser, Boston; and Sayegh et al. (2001) Current and Future Immunosuppressive Therapies Following Transplantation, Kluwer Academic Publishers.

Although improved therapeutic strategies have been developed, the adverse side effects associated with immunosuppressive agents remain a significant challenge. Nephrotoxicity is a serious complication of many immunosuppressive therapies, particularly, those that utilize calcineurin inhibitors.

Acute cyclosporine (CsA) toxicity causes nephritis characterized by a decrease in glomerular filtration rate (GFR) and renal blood flow, hypomagnesemia, and tubular injury. Likewise, chronic CsA toxicity results in a progressive state of renal dysfunction characterized by interstitial fibrosis, tubular atrophy, and vascular changes such as arterial ischemia. These changes ultimately lead to end-stage renal disease and renal failure. Nephrotoxicity was, for example, observed in graft recipients treated with tacrolimus (see, e.g., English et al. (2002) Am. J. Transplant., 2:769-273) and sirolumus (see, e.g., Fervenza et al. (2004) Nephrol. Dial. Transplant., 19(5):1288-1292).

Recent studies have implicated Transforming Growth Factor-β (TGF-β) as a mediator of both immunosuppressive activity and/or nephrotoxicity of certain immunosuppressants, including CsA, tacrolimus, and rapamycin (Khanna et al. (2000) Transplantation, 70(4):90-694). Blocking TGF-β in non-transplant models of CsA nephrotoxicity by administration of an anti-TGF-β antibody was shown to substantially reduce overall tissue fibrosis (Khanna et al. (1999) Transplantation, 67:882-889; Islam (2001) 59:498-506; Ling et al. (2003) J. Am. Soc. Nephrol., 14:377-388), however, it also inhibits the immunosuppressive effects of the agents.

A number of experimental strategies have been examined with the goal of reducing nephrotoxicity while retaining immunosuppression in this class of drugs. Agents that may moderate nephrotoxicity by a TGF-β-related but indirect mechanism include: mycophenolate mofetil (MMF) (Shihab et al. (2003) Am. J. Transplant., 3:1550-1559), spironolactone (Feria et al. (2003) Kidney Int., 63:43-52), losartan (Yang et al. (2003) Transplantation, 75:309-315), vitamin E (Jenkins et al. (2001) Transplantation, 71:331-334), pirfenidone (Shihab (2002) Am. J. Transplantation, 2:111-119), and angiotensin receptor blockade (Boffa et al. (2003) J. Am. Soc. Nephrol., 14:1132-1144). However, none are completely satisfactory.

Therefore, there exists a need for treatment modalities that would allow reduced nephrotoxicity of CsA or other immunosuppressive agents, while maintaining their immunosuppressive activity.

SUMMARY OF THE INVENTION

TGF-β mediates both the immunosuppressive and nephrotoxic effects of certain immunosuppressive agents. Because of this dual activity, prior to the present invention it was not known whether or not an adjunct therapy with a direct TGF-β antagonist, such as, for example, an anti-TGF-β antibody, could sufficiently reduce the nephrotoxic effects of these agents without, at the same time, substantially interfering with their immunosuppressive activity.

The present invention provides methods and compositions for reducing nephrotoxicity of immunosuppressive agents, particularly in the context of organ transplantation or an autoimmune disease. Accordingly, the methods are useful for treating patients undergoing an immunosuppressive therapy to prevent graft rejection or to treat an autoimmune disease.

The present invention is based, in part, on the discovery and demonstration that low, but not high, doses of an anti-TGF-β antibody mitigate CsA-mediated nephrotoxicity without substantially interfering with CsA's immunosuppressive activity as judged by allograft survival.

In experiments conducted in connection with the invention, CsA-immunosuppressed rats that received cardiac graft transplants were administered an anti-TGF-β antibody. Rats treated with the anti-TGF-β antibody at a lower dose (1 mg/kg) demonstrated a reduction in nephrotoxic effects, while their graft survival was similar to the controls treated with CsA alone. Under the same conditions, a higher dose (2.5 mg/kg) of the anti-TGF-β antibody almost completely abolished immunosuppressive effects of CsA.

Accordingly, the present invention provides an adjunct therapy for amelioration of nephrotoxic side effects of those immunosuppressive agents that mediate their immunosuppressive activity at least in part via upregulation of TGF-β. Typically, such agents induce expression of TGF-β upon administration. Examples of such immunosuppressive agents include, but are not limited to, cyclosporine, tacrolimus, and sirolimus. The invention provides methods of treating or preventing nephritis induced by such agents.

The methods of the invention include administering a TGF-β antagonist to a mammal in need of immunosuppression who is treated with an immunosuppressive agent. The TGF-β antagonist is administered in a therapeutically effective amount sufficient to alleviate the nephrotoxic effects of the immunosuppressive agent without substantially interfering with immunosuppressive activity of the agent.

The dose(s) at which a TGF-β antagonist is administered is/are such that the reduction of nephrotoxic effects of the immunosuppressive agent is achieved while maintaining therapeutic efficacy of the immunosuppressive agent. Typically, the dose at which a TGF-β antagonist is administered is lower (e.g., by 20%) than the recommended dose that would be administered to treat nephritis in the absence of the immunosuppressive agent.

In some embodiments, a TGF-β antagonist is a direct TGF-β antagonist, such as, for example, an anti-TGF-β antibody, an anti-TGF-β receptor antibody, or a soluble TGF-β receptor. In specific embodiments, the TGF-β antagonist is the anti-TGF-β antibody 1D11, the anti-TGF-β antibody CAT192, or the anti-TGF-β antibody CAT152, or a derivative of either of those antibodies. In nonlimiting preferred embodiments, the TGF-β antagonist is a human pan-specific antibody such as PET1073G12, PET 1074B9 or PET1287A10, as disclosed in U.S. provisional application No. 60/651,343.

The invention further provides methods for detecting nephrotoxicity an immunosuppressive agent as well as methods for evaluating a test compound or composition for the ability to reduce nephrotoxic effects of an immunosuppressive agent. Such methods comprise obtaining a biological sample from a mammal treated with an immunosuppressive agent and determining the level of expression of one or more molecules selected from the group consisting of TGF-β, NOX-1, $p22^{phox}$, RAC-1, SOD, and TRX. Expression levels indicate nephrotoxicity of an immunosuppressive agent and/or the effectiveness of the compound or composition in reducing the same.

BRIEF DESCRIPTION OF THE FIGURES

FIG. 5 demonstrates the effect of TAC and/or anti-TGF-β antibodies on renal function in renal transplant recipients.

BRIEF DESCRIPTION OF THE SEQUENCES

Figure 1:
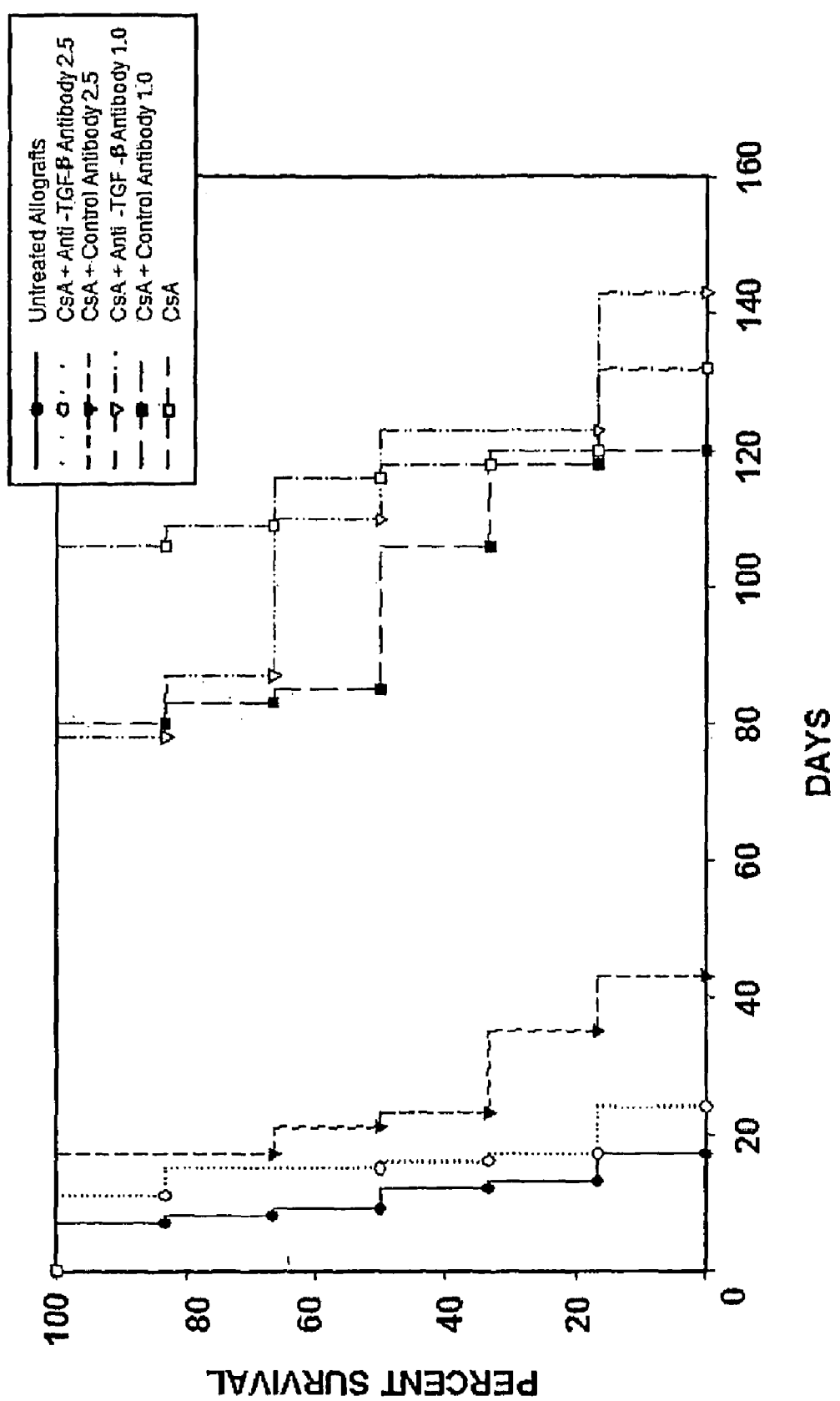
FIG. 1 shows a Kaplan-Meier graph indicating a negative effect of a high dose of an anti-TGF-β antibody on the immunosuppressive effect of CsA and a beneficial effect of a lower dose of the antibody on nephrotoxicity. Along with CsA, recipients were also treated with anti-TGF-β or control antibody (2.5 or 1.0 mg/kg each) three times a week. Groups included: isografts, untreated allografts, CsA treated allografts, CsA+control antibody (2.5 mg/kg), CsA+anti-TGF-β antibody (2.5 mg/kg), CsA+control antibody (1.0 mg/kg), CsA+anti-TGF-β antibody (1.0 mg/kg), and isotype antibody controls. Anti-TGF-β antibody at the 2.5 mg/kg dose, but not 1.0 mg/kg, abrogated the immunosuppressive effects of CsA. CsA+control antibody treated recipients did not exhibit graft rejection but were sacrificed for comparison with anti-TGF-β antibody treated recipients.

SEQ ID NOs:1-12 represent PCR primers used for evaluating gene expression levels in kidneys as described in the Examples.

DETAILED DESCRIPTION OF THE INVENTION

The methods of the invention include administering a TGF-β antagonist to a mammal being treated with an immunosuppressive agent. The methods of the invention reduce the nephrotoxicity associated with treatment with an immunosuppressant agent, but do not substantially reduce the immunosuppressive activity of the agent.

TGF-β Antagonists

TGF-β is a disulfide linked dimer that is synthesized as a preprotein of about 400 amino acids (aa) which is cleaved prior to secretion to produce mature TGF-β. The N-terminal cleavage fragment, known as the "latency-associated peptide" (LAP), may remain noncovalently bound to the dimer, thereby inactivating TGF-β. TGF-β, isolated in vivo, is found predominantly in this inactive, "latent" form, i.e., associated with LAP. Latent TGF-β complex may be activated in several ways, for example, by binding to a cell surface receptor called the cation-independent mannose-6-phosphate/insulin-like growth factor II receptor. Binding occurs through mannose-6-phosphate residues attached at glycosylation sites within LAP. Upon binding to the receptor, TGF-β is released in its mature form. Mature, active TGF-β is then free to bind to its receptor and exert its biological functions. The major TGF-β-binding domain in the type II TGF-β receptor has been mapped to a 19 amino acid sequence (Demetriou et al. (1996) J. Biol. Chem., 271:12755).

The term "TGF-β," as used herein, refers to any one or more isoforms of TGF-β. Likewise, the term "TGF-β receptor," unless otherwise indicated, refers to any receptor that binds at least one TGF-β Isoform. Currently, there are five known isoforms of TGF-β (TGF-β1 to TGF-β5), all of which are homologous among each other (60-80% identity), form homodimers of about 25 kDa, and act upon common TGF-β receptors (TβR-I, TβR-II, TβR-IIB, and TβR-III). TGF-β1, TGF-β2, and TGF-β3 are found in mammals. The structural and functional aspects of TGF-β as well as TGF-β receptors are well known in the art (see, for example, Cytokine Reference, eds. Oppenheim et al., Academic Press, San Diego, Calif., 2001). TGF-β is remarkably conserved among species. For example, the amino acid sequences of rat and human mature TFG-β1s are nearly identical. Thus, antagonists of TGF-β are expected to have a high species cross-reactivity.

The term "TGF-β antagonist" and its cognates such as "inhibitor," "neutralizing," and "downregulating" refer to a compound (or its property as appropriate), which acts as an antagonist of biological activity of TGF-β. A TGF-β antagonist may, for example, bind to and neutralize the activity of TGF-β; decrease TGF-β expression levels; affect stability or conversion of the precursor molecule to the active, mature form; interfere with the binding of TGF-β to one or more receptors; or it may interfere with intracellular signaling of a TGF-β receptor. The term "direct TGF-β antagonist" generally refers to any compound that directly downregulates the biological activity of TGF-β. A molecule "directly downregulates" the biological activity of TGF-β if it downregulates the activity by interacting with a TGF-β gene, a TGF-β transcript, a TGF-β ligand, or a TGF-β receptor.

Methods for assessing neutralizing biological activity of TGF-β and TGF-β antagonists are known in the art. Examples of some of the more frequently used in vitro bioassays include the following:

(1) induction of colony formation of NRK cells in soft agar in the presence of EGF (Roberts et al. (1981) Proc. Natl. Acad. Sci. USA, 78:5339-5343);

(2) induction of differentiation of primitive mesenchymal cells to express a cartilaginous phenotype (Seyedin et al. (1985) Proc. Natl. Acad. Sci. USA, 82:2267-2271);

(3) inhibition of growth of Mv1Lu mink lung epithelial cells (Danielpour et al. (1989) J. Cell. Physiol., 138:79-86) and BBC-1 monkey kidney cells (Holley et al. (1980) Proc. Natl. Acad. Sci. USA, 77:5989-5992);

(4) inhibition of mitogenesis of C3H/HeJ mouse thymocytes (Wrann et al. (1987) EMBO J., 6:1633-1636);

(5) inhibition of differentiation of rat L6 myoblast cells (Florini et al. (1986) J. Biol. Chem., 261:16509-16513);

(6) measurement of fibronectin production (Wrana et al. (1992) Cell, 71:1003-1014);

(7) induction of plasminogen activator inhibitor I (PAI-1) promoter fused to a luciferase reporter gene (Abe et al. (1994) Anal. Biochem., 216:276-284);

(8) sandwich enzyme-linked immunosorbent assays (Danielpour et al. (1989) Growth Factors, 2:61-71); and (9) cellular assays described in Singh et al. (2003) Bioorg. Med. Chem. Lett., 13(24):4355-4359.

Examples of TGF-β antagonists that may be used in the methods of the present invention, include but are not limited to: monoclonal and polyclonal antibodies directed against one or more isoforms of TGF-β (U.S. Pat. No. 5,571,714; WO 97/13844; WO 00/66631; dominant negative and soluble TGF-β receptors or antibodies directed against TGF-β receptors (Flavell et al. (2002) Nat. Rev. Immunol., 2(1):46-53); U.S. Pat. No. 5,693,607; U.S. Pat. No. 6,001,969; U.S. Pat. No. 6,008,011; U.S. Pat. No. 6,010,872; WO 92/00330; WO 93/09228; WO 95/10610; and WO 98/48024; LAP (WO 91/08291); LAP-associated TGF-β (WO 94/09812); TGF-β-binding glycoproteins/proteoglycans such as fetuin (U.S. Pat. No. 5,821,227); decorin, biglycan, fibromodulin, lumican, and endoglin (U.S. Pat. No. 5,583,103; U.S. Pat. No. 5,654,270; U.S. Pat. No. 5,705,609; U.S. Pat. No. 5,726,149; U.S. Pat. No. 5,824,655; U.S. Pat. No. 5,830,847; U.S. Pat. No. 6,015,693; WO 91/04748; WO 91/10727; WO 93/09800; and WO 94/10187); mannose-6-phosphate or mannose-1-phosphate (U.S. Pat. No. 5,520,926); prolactin (WO 97/40848); insulin-like growth factor II (WO 98/17304); extracts of plants, fungi, and bacteria (EU 813875; JP 8119984; and U.S. Pat. No. 5,693,610); antisense oligonucleotides (U.S. Pat. No. 5,683,988; U.S. Pat. No. 5,772,995; U.S. Pat. No. 5,821,234; U.S. Pat. No. 5,869,462; and WO 94/25588); proteins involved in TGF-β signaling, including SMADs and MADs (EP 874046; WO 97/31020; WO 97/38729; WO 98/03663; WO 98/07735; WO 98/07849; WO 98/45467; WO 98/53068; WO 98/55512; WO 98/56913; WO 98/53830; WO 99/50296; U.S. Pat. No. 5,834,248; U.S. Pat. No. 5,807,708; and U.S. Pat. No. 5,948,639), Ski and Sno (Vogel (1999) Science, 286:665 and Stroschein et al. (1999) Science, 286:771-774); and any mutants, fragments, or derivatives of the above-identified molecules that retain the ability to directly inhibit the biological activity of TGF-β.

Examples of TGF-β antagonists that may be used in the methods of the present invention include small molecule inhibitors, such as serine/threonine kinase inhibitors, for example, those described in WO 04/21989; WO 03/87304; WO 04/26871; WO 04/26302; WO 04/24159, U.S. Pat. No. 6,184,226; WO 03/97639; and WO 04/16606.

In some embodiments, the TGF-β antagonist is a direct TGF-β antagonist, for example, an antibody that blocks TGF-β binding to its receptor.

The term "antibody," as used herein, refers to an immunoglobulin or a part thereof, and encompasses any polypeptide comprising an antigen-binding site regardless of the source, method of production, and other characteristics. The term includes but is not limited to polyclonal, monoclonal, monospecific, polyspecific, humanized, human, single-chain, chimeric, synthetic, recombinant, hybrid, mutated, and CDR-grafted antibodies. The term "antigen-binding domain" refers to the part of an antibody molecule that comprises the area specifically binding to or complementary to, a part or all of an antigen. Where an antigen is large, an antibody may only bind to a particular part of the antigen. The "epitope," or "antigenic determinant" is a portion of an antigen molecule that is responsible for specific interactions with the antigen-binding domain of an antibody. An antigen-binding domain may comprise an antibody light chain variable region ($V_L$) and an antibody heavy chain variable region ($V_H$). An antigen-binding domain may be provided by one or more antibody variable domains (e.g., an Fd antibody fragment consisting of a $V_H$ domain, an Fv antibody fragment consisting of a $V_H$ domain and a $V_L$ domain, or an scFv antibody fragment consisting of a $V_H$ domain and a $V_L$ domain joined by a linker). The term "anti-TGF-β antibody," or "antibody against at least one isoform of TGF-β," refers to any antibody that specifically binds to at least one epitope of TGF-β. The terms "TGF-β receptor antibody" and "antibody against a TGF-β receptor" refer to any antibody that specifically binds to at least one epitope of a TGF-β receptor (e.g., type I, type II, or type III).

Antibodies useful in the methods of the invention are such that they specifically bind to at least one isoform of TGF-β or to the extracellular domain of at least one TGF-β receptor. The terms "specific interaction," or "specifically binds," or their cognates, as used herein, mean that two molecules form a complex that is relatively stable under physiologic conditions. Specific binding is characterized by a high affinity and a low to moderate capacity. Nonspecific binding usually has a low affinity with a moderate to high capacity. Typically, the binding is considered specific when the affinity constant $K_a$ is higher than $10^6 M^{-1}$, or preferably higher than $10^8 M^{-1}$.

In some other embodiments, the anti-TGF-β antibody specifically binds at least one isoform of TGF-β selected from the group consisting of TGF-β1, TGF-β2, and TGF-β3. In yet other embodiments, the anti-TGF-β antibody specifically binds to at least: (a) TGF-β1, TGF-β2, and TGF-β3 ("pan-neutralizing antibody"); (b) TGF-β1 and TGF-β2; (c) TGF-β1 and TGF-β3; and (d) TGF-β2 and TGF-β3. In various embodiments, the affinity constant $K_a$ of the TGF-β antibody for at least one isoform of TGF-β, which it specifically binds, is preferably greater than $10^6 M^{-1}$, $10^7 M^{-1}$, $10^8 M^{-1}$, $10^9 M^{-1}$, $10^{10} M^{-1}$, $10^{11} M^{-1}$, or $10^{12} M^{-1}$. In further embodiments, the antibody of the invention specifically binds to a protein substantially identical to human TGF-β1, TGF-β2, and/or TGF-β3. Also contemplated for use in humans are humanized and fully human forms and derivatives of nonhuman antibodies derived from any vertebrate species described in the cited references. Producing such variants is well within the ordinary skill of an artisan (see, e.g., Antibody Engineering, ed. Borrebaeck, 2nd ed., Oxford University Press, 1995).

In nonlimiting illustrative embodiments, the anti-TGF-β antibody is the murine monoclonal antibody 1D11 produced by the hybridoma 1D11.16 (ATCC Deposit Designation No. HB 9849, also described in U.S. Pat. Nos. 5,571,714; 5,772,998; and 5,783,185). The sequence of the 1D11 heavy chain variable region is available under accession No. AAB46787. Thus, in related embodiments, the anti-TGF-β antibody is a derivative of 1D11, e.g., an antibody comprising CDR sequences identical to those in AAB46787, such as a humanized antibody. In further embodiments, the anti-TGF-β antibody is a fully human recombinant antibody generated by phage display, such as CAT192 and CAT152 described in WO 00/66631, U.S. Pat. No. 6,492,497, and U.S. Patent Application Publications Nos. 2003/0091566 and 2003/0064069, or an antibody comprising the CDR sequences disclosed therein. In yet further embodiments, the anti-TGF-β antibody is an antibody produced by guided selection from 1D11, CAT192, or CAT152.

In nonlimiting preferred embodiments, the anti-TGF-β antibody is a human pan-specific antibody such as PET1073G12, PET1074B9, or PET1287A10, as disclosed in U.S. provisional application No. 60/651,343. In a highly preferred embodiment, a VH domain is provided with the amino acid sequence of SEQ ID NO: 13, this being termed "PET1073G12 VH domain," or SEQ ID NO: 15, this being termed "PET1074B9 VH domain," or SEQ ID NO: 17, this being termed "PET1287A10 VH domain."

In a further highly preferred embodiment, a VL domain is provided with the amino acid sequence of SEQ ID NO: 14, this being termed "PET1073G12 VL domain," or SEQ ID NO: 16, this being termed "PET1074B9 VL domain," or SEQ ID NO: 18, this being termed "PET1287A10 VL domain." A highly preferred embodiment provided in accordance with the present invention is composed of the PET1073G12 VH domain, SEQ ID NO: 13, and the PET1073G12 VL domain SEQ ID NO: 14. Another highly preferred embodiment provided in accordance with the present invention is composed of the PET1074B9 VH domain, SEQ ID NO: 15, and the PET1074B9 VL domain, SEQ ID NO: 16. Another highly preferred embodiment provided in accordance with the present invention is composed of the PET1287A10 VH domain, SEQ ID NO: 17, and the PET1287A10 VL domain, SEQ ID NO: 18. These or any other antibody antigen-binding site provided in accordance with the present invention may be provided within any desired antibody molecule format, e.g. scFv, Fab, IgG1, IgG4, dAb etc.

In a further highly preferred embodiment, the present invention provides an IgG4 antibody molecule comprising the PET1073G12. PET1074B9 or PET1287A10 VH domain, preferably also comprising the corresponding PET1073G12, PET1074B9 or PET1287A10 VL domain.

While the 1D11 antibody specifically binds all three mammalian isoforms of TGF-β, CAT192 specifically binds TGF-β1 only. The antigen affinities for 1D11 and CAT192 are approximately 1 nM and 8.4 pM, respectively. The epitopes for 1D11 (Dasch et al. (1998) J. Immunol., 142:1536-1541) and CAT192 have been mapped to the C-terminal portion of mature TGF-β.

Immunosuppressive Agents

The present invention provides an adjunct therapy for amelioration of nephrotoxic side effects of those immunosuppressive agents that mediate their immunosuppressive activity, at least in part, via upregulation of TGF-β. The terms "immunosuppressive agent," "immunosuppressant," and "immunodepressant" as used herein, refer to a compound or composition that induces immunosuppression, i.e., it prevents or interferes with the development of an immunologic response. Example of immunosuppressive agents include, but are not limited to, Sandimmune™ (cyclosporine); Prograf™, Protopic™ (tacrolimus); Rapamune™, Neoral™ (sirolimus); FTY720; Certican™ (everolimus, rapamycin derivative); Campath™-1H (alemtuzumab, anti-CD52 antibody); Rituxan™ (rituximab, anti-CD20 antibody); OKT4; LEA29Y (BMS-224818, CTLA4Ig); indolyl-ASC (32-indole ether derivatives of tacrolimus and ascomycin); Imuran™ (azathioprine); Atgam™ (antithymocyte/globuline); Orthoclone™ (OKT3; muromonab-CD3); Cellcept™ (mycophenolate mofetil); Zenapax™ (daclizumab), Cytoxan™ (cyclophosphamide), prednisone, prednisolone and other corticosteroids malononitrilamides (MNAs (leflunomide, FK778, FK779)), and 15-deoxyspergualin (DSG).

Methods for assessing immunosuppressive activity of an agent are known in the art. As described in the Examples, the length of the survival time of the transplanted organ in vivo with and without pharmacological intervention serves as a quantitative measure for the suppression of the immune response. In vitro assays may also be used, for example, a mixed lymphocyte reaction (MLR) assay (see, e.g., Fathman et al. (1977) J Immunol., 118(4):1232-1238); a CD3 assay (specific activation of immune cells via an anti-CD3 antibody (e.g., OKT3)) (see, e.g., Khanna et al. (1999) Transplantation, 67(6):882-889 and Khanna et al. (1999) Transplantation, 67(7):S58); and an IL-2R assay (specific activation of immune cells with the exogenously added cytokine IL-2) (see, e.g., Farrar et al., (1981) J. Immunol., 126(3):1120-1125).

The present invention is of particular use with nephrotoxic immunosuppressive agents that mediate their immunosuppressive activity, at least in part, via upregulation of TGF-β. Such agents may induce acute or chronic nephritis upon administration. Typically, the induction is correlated with elevated expression of TGF-β upon administration of the agent. The invention provides methods of treating or preventing nephritis induced by such agents.

Whether a specific immunosuppressive agent mediates its immunosuppressive activity via upregulation of TGF-β may be determined using methods known in the art, e.g., as described in the Examples. Specific examples of agents that mediate their immunosuppressive activity via upregulation of TGF-β include, but are not limited to, cyclosporine, tacrolimus, and sirolimus (see, e.g., Khanna (2000) Transplantation, 70(4): 690-694; Khanna et al. (1999) Transplantation, 67(7): S84; and Khanna et al. (1999) Transplantation, 67(6):882-889).

Cyclosporine A (CAS No. 59865-13-3; U.S. Pat. No. 3,737,433) is designated as [R-[RR*(E){]cyclic(L-alanyl-D-alanyl-N-methyl-L-leucyl-N-methyl-L-leucyl-N-methyl-L-valyl-3-hydroxy-N,4-dimethyl-L-2-amino-6-octenoyl-L-α-amino-butyryl-N-methylgiycyl-N-methyl-L-leucyl-L-valyl-N-methyl-L-leucyl). Its immunosuppressive effect has been known since 1972 (Borel, J. F.: Cyclosporine. In: Dale et al. (eds.): Textbook of Immunology (3rd ed.), Blackwell Scient. Publ. Oxford 1994, pp 320-329). A number of other cyclosporines and their derivatives and analogs that exhibit immunosuppressive activity are known. Cyclosporines and their formulations are described, for example, in 2004 Physicians' Desk Reference® (2003) Thomson Healthcare, 58th ed., and U.S. Pat. Nos. 5,766,629; 5,827,822; 4,220,641; 4,639,434; 4,289,851; and 4,384,996; 5,047,396; 4,388,307; 4,970,076; and 4,990,337; 4,822,618; 4,576,284; 5,120,710; and 4,894,235.

Tacrolimus (FK506) is a macrolide which exerts effects largely similar to CsA, both with regard to its molecular mode of action and its clinical efficacy (Liu (1993) Immunol. Today, 14: 290-295; Schreiber et al. (1992) Immunol. Today, 13:136-142); However, these effects are exhibited at doses that are 20 to 100 times lower than CsA (Peters et al. (1993) Drugs, 46:746-794). Chemically, tacrolimus is [3S-[3R*[E (1S*,3S*,4S*)], 4S*,5R*,8S*,9E, 12R*,14R*,15S*,16R*, 18S*,19S*,26aR*]]-5,6,8,11,12,13,14,15,16,17,18,19,24, 25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4]oxaazacyclotricosine-1,7,20,21 (4H, 23H)-tetrone, monohydrate. Tacrolimus and its formulations are described, for example, in 2004 Physicians' Desk Reference® (2003) Thomson Healthcare, 58th ed., and U.S. Pat. Nos. 4,894,366; 4,929,611; and 5,164,495.

Sirolimus (rapamycin) is an immunosuppressive lactam macrolide produceable, for example, by *Streptomyces hygroscopicus*. Chemically, sirolimus is (3S,6R,7E,9R,10R,12R, 14S,15E,17E,19E,21S,23S,26R,27R,34aS)-9,10,12,13,14, 21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8, 12,14,20,26-hexamethyl-23,27-epoxy-3H-pyrido[2,1-c][1, 4]oxaazacyclohentri-acontine-1,5,11,28,29 (4H,6H,31H)-pentone. The structure of sirolimus is given, for example, in Kesseler et al. (1993) Helv. Chim. Acta, 76:117.

Numerous derivatives of sirolimus and its analogs and their formulations are known and described, for example, in 2004 Physicians' Desk Reference® (PDR) (2003) Thomson Healthcare, 58th ed., WO 94/02136, WO 94/09010, WO 92/05179, WO 93/11130, WO 94/02385, WO 95/14023, WO 94/02136 and U.S. Pat. Nos. 5,258,389; 5,118,677; 5,118, 678; 5,100,883; 5,151,413; 5,120,842; and 5,256,790.

Uses and Methods of Administration

The methods of the invention include administering a TGF-β antagonist to a mammal with a nephrotoxic immunosuppressive agent.

Mammals treated according to the methods of the invention include but are not limited to humans and other primates, rodents (e.g., mice, rats), rabbits, cats, dogs, cows, and pigs.

The mammals treated according to the methods of the invention include patients in need of immunosuppression, for example, patients with an autoimmune disease. Examples of autoimmune diseases that may be amenable to the methods of the invention include systemic lupus erythematosus, rheumatoid arthritis, multiple sclerosis, Crohn's disease (inflammatory bowel disease), type 1 diabetes mellitus, myasthenia gravis, psoriasis, Graves disease, Berger's disease, scleroderma, Sjogren syndrome, ankylosing spondylitis, Goodpasture syndrome, autoimmune hemolytic anemia, Addison disease, Hashimoto thyroiditis, idiopathic thrombocytopenic purpura, pernicious anemia, and spontaneous infertility.

The mammals treated according to the methods of the invention further include patients in need of immunosuppression, for example, patients with an organ or tissue transplant undergoing an immunosuppressive therapy. "Transplant" refers to any grafts or tissue or whole or parts of organs, or cells that are foreign to a recipient (host). Examples of transplants include but are not limited to heart, kidney, lung, liver, cornea, bone marrow, blood vessel and islet cell transplants. A transplant can be either from the same species as the recipient (allotransplant) or from species other than the recipient's (xenotransplant).

Immunosuppressive management of the transplantation patient begins with the induction phase, perioperatively and immediately after transplantation. Induction therapy is a course of intensive immunosuppression for about two weeks immediately post-operatively (though often started immediately preoperatively) with the aim of 'switching off' the immune system after transplantation to reduce the likelihood of accelerated rejection and acute rejection. Maintenance therapy then continues for the life of the allograft. Induction and maintenance strategies may use different immunosuppressants at specific doses or at doses adjusted to achieve therapeutic levels that provide optimal graft survival. In certain embodiments, a TGF-β antagonist is administered to a patient during the induction phase of immunosuppression therapy, during the maintenance phase, or both.

The TGF-β antagonist is administered in a therapeutically effective amount sufficient to alleviate nephrotoxic effects of the immunosuppressive agent without substantially interfering with immunosuppressive activity of the agent.

The term "sufficient to alleviate nephrotoxic effects" refers to slowing or reversing loss of renal function or deterioration of renal structure due to an immunosuppressive agent. "Renal function" refers to the ability of a kidney to perform its physiological functions such as pressure filtration, selective reabsorption, tubular secretion, and/or systemic blood pressure regulation.

Methods for assessing renal function are well known in the art and include, but are not limited to, measurements of blood systemic and glomerular capillary pressure, proteinuria (e.g., albuminurea), microscopic and macroscopic hematurea, serum creatinine level (e.g., one formula for estimating renal function in humans equates a creatinine level of 2.0 mg/dl to 50 percent of normal kidney function and 4.0 mg/dl to 25 percent), decline in the glomerular filtration rate (GFR) (e.g., rate of creatinine clearance), and degree of tubular damage.

For a detailed review of renal function and disease states, see The Kidney Physiology and Pathophysiology, eds. Seldin et al., 3rd ed., Lippincott Williams & Wilkins Publishers, 2000. Normally, less than 0.15 g of protein is excreted into the urine per 24 hour period. Almost all types of kidney disease cause mild (up to 500 mg per day) to moderate (up to 4 g per day) protein leakage into the urine. The normal concentration of albumin in the urine is less than 1.0 mg/dl. Generally, 30-300 mg/dl urinary albumin is considered microalbuminuria, and 300 mg/dl and up is considered macroalbuminuria. The normal values of serum creatinine are 0.6-1.5 mg/dl for men and 0.6-1.1 mg/dl for women. The relationship between creatinine levels, renal function, and the stage of renal disease is shown in Table 1.

TABLE 1

| Creatinine level (mg/dl) | Estimated reduction of renal function | Stage of renal disease |
|---|---|---|
| 0.6-1.5 | Up to 25% | Reduced or diminished renal reserve |
| >1.5 | >50% | Renal insufficiency |
| 4.8 | 75% | Renal failure |
| 10 | 90% | End-stage renal disease |

The methods of the invention may be particularly useful in patients with renal insufficiency, renal failure, or end-stage renal disease attributable at least in part to a nephrotoxicity of an immunosuppressive agent. In patients undergoing an immunosuppressive therapy, other indications may include creatinine clearance levels of lower than 97 (men) and 88 (women) ml/min, blood urea of 20-25 mg/dl or higher. Furthermore, the treatment may be useful in patients with microalbuminuria, macroalbuminuria, and/or proteinuria levels of over 1, 2, 3, 4, 5, 6, 7, 8, 9, or 10 g or more per a 24 hour period, and/or serum creatinine levels of about 1.0, 1.5, 2.0, 2.5, 3, 3.5, 4.0, 4.5, 5, 5.5, 6, 7, 8, 9, 10 mg/dl or higher.

The methods of the invention can be used to slow or reverse the progression of renal disease in patients whose renal function is below normal by 25%, 40%, 50%, 60%, 75%, 80%, 90% or more, relative to control subjects. In some embodiments, the methods of the invention slow the loss of renal function by at least 10%, 20%, 30%, 40%, 50%, 60%, 70%, 80%, 90%, 100% or more, relative to control subjects. In other embodiments, the methods of the invention improve the patient's serum creatinine levels, proteinuria, and/or urinary albumin excretion by at least 10%, 20%, 30%, 40%, 50%, 60%, 70%, or more, relative to control subjects. Nonlimiting illustrative methods for assessing renal function are described herein and, for example, in WO 01/66140.

Methods for assessing deterioration of renal structure are also well known. Illustrative methods are described in the Examples. Such methods include renal imaging (e.g., MRI, ultrasound), or histological evaluation of renal biopsy. In some embodiments, the methods of the invention reduce deterioration of renal structure as judged, for example, by the extent of tubulointerstitial or glomerular damage and/or the degree of renal fibrosis (e.g., deposition of collagen and fibronectin). In some embodiments, the methods of the invention improve the structural changes by at least 10%, 20%, 30%, 40%, 50%, 60%, 70%, or more.

A treating physician will determine the exact dosages and regimens of the TGF-β antagonist. Generally, dosages of the TGF-β antagonist should be such that the risk of rejection due to the administration of the antagonist is increased by no more than therapeutically acceptable, (i.e., it does not substantially interfere with the immunosuppressive activity of the immunosuppressant). Furthermore, the dosage should be such that the reduction of nephrotoxic effects of the immunosuppressive agent is therapeutically acceptable. For example, an increase of rejection rate in the maintenance phase by no more than 5, 10, 15, 20, 25, 30, 40 or 50% may be therapeutically acceptable.

In the methods of the invention, a TGF-β antagonist is generally administered at a therapeutically effective dose which is lower than the dose recommended to be administered in the absence of the immunosuppressive agent. In certain embodiments, this dose is lower than the dose recommended to treat nephritis in the absence of the immunosuppressive, agent by at least 30%, 40%, 50%, 60%, 70%, or more. In some embodiments, the therapeutically effective dose of a TGF-β antagonist is at least 30%, 40%, 50%, 60%, 70%, or more, below the maximal therapeutically effective dose administered in the absence of the immunosuppressive agent.

In certain embodiments, a TGF-β antagonist is administered at a dose at below the dose equivalent to 2, 1.9, 1.8, 1.6, 1.5, 1.4, 1.3, 1.2, or 1.0 mg/kg body weight of the 1D11 antibody when administered in rodents, e.g., under conditions such as described in the Examples. A treating physician will determine the exact dosages and regimens for TGF-β antagonists and adjunct therapeutics. As a starting point, a therapeutically effective dose of an anti-TGF-β antibody, an anti-TGF-β receptor antibody, a soluble TGF-β receptor, or another TGF-β antagonist may be in the range of 0.005 to 50, 0.05 to 5, or 0.5 to 5 mg/kg/day.

Therapeutically effective dosages achieved in one animal may be converted for use in another animal, including humans, using conversion factors known in the art (see, e.g., Freireich et al. (1966) Cancer Chemother. Reports, 50(4): 219-244 and Table 2 for equivalent surface area dosage factors).

TABLE 2

| | To: | | | | |
|---|---|---|---|---|---|
| From: | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

"Administration" is not limited to any particular formulation, delivery system, or route and may include, for example, parenteral (including subcutaneous, intravenous, intramedullary, intraarticular, intramuscular, or intraperitoneal injection) rectal, topical, transdermal, or oral (for example, in capsules, suspensions, or tablets). Administration to an individual may occur in a single dose or in repeat administrations, and in any of a variety of pharmaceutical compositions containing physiologically acceptable salt forms, and/or with an acceptable pharmaceutical carrier and/or additive as part of a pharmaceutical composition. Physiologically acceptable salt forms and standard pharmaceutical formulation techniques and excipients are known (see, e.g., Physicians' Desk Reference® 2003, 57th ed., Medical Economics Company, 2002; and Remington: The Science and Practice of Pharmacy, eds. Gennado et al., 20th ed, Lippincott, Williams & Wilkins, 2000).

Administration of an antagonist to an individual may also be accomplished by means of gene therapy, wherein a nucleic acid sequence encoding the antagonist is administered to the patient in vivo or to cells in vitro, which are then introduced into a patient, and the antagonist (e.g., antisense RNA, soluble TGF-β receptor) is produced by expression of the product encoded by the nucleic acid sequence. Methods for gene therapy to deliver TGF-β antagonists are described (see, e.g., Fakhrai et al. (1996) Proc. Nat. Acad. Sci. U.S.A., 93:2909-2914). Administration of a TGF-β antagonist is effected by gene transfer using a vector comprising cDNA encoding the antagonist, most preferably cDNA encoding the extracellular domain of TGF-β type II (rsTGFBIIR) or type III receptor (rsTGFBIIIR), as described in, e.g., U.S. Patent Application Publication No. 2003/0180301.

A TGF-β antagonist and an immunosuppressive agent may be administered concurrently or consecutively over overlapping or nonoverlapping intervals. In the sequential administration, the TGF-β antagonist and the immunosuppressive agent can be administered in any order. The antagonists are administered as the sole active compound or in combination with another compound or composition. Specific dosages of immunosuppressive agents as indicated the Physicians' Desk Reference® may be used.

The invention further provides methods for detecting nephrotoxicity of an immunosuppressive agent (e.g., CsA, TAC, rapamycin, or another immunosuppressive agent) in mammal who is in need of immunosuppression and has been administered the agent for immunosuppression. The methods comprise obtaining a biological sample from the mammal and determining the level of expression of one or more molecules selected from the group consisting of TGF-β, NOX-1, $p22^{phox}$, RAC-1, SOD, and TRX. The invention further provides methods for detecting nephrotoxicity of an immunosuppressive agent (e.g., CsA, TAC, rapamycin, or another immunosuppressive agent) in mammal who is in need of immunosuppression and has been administered the agent for immunosuppression.

The invention yet further provides methods for evaluating a test compound or composition (e.g., a TGF-beta antagonist such as an anti-TGF-β antibody) for the ability to reduce nephrotoxic effects of an immunosuppressive agent. These methods comprise obtaining a biological sample from a mammal who has been administered both the immunosuppressive agent and the test compound or composition of interest and determining the level of expression of one or more molecules (one, two, three, four, five, or all six) selected from the group consisting of TGF-β, NOX-1, $p22^{phox}$, RAC-1, SOD, and TRX.

Expression levels above appropriate control(s) indicate nephrotoxicity of an immunosuppressive agent and/or the effectiveness of the compound or composition in reducing the same. For example, expression levels that differ by 20, 30, 40, or 5 percent, or at least 2-, 4-, 5-, or 10-fold from the appropriate control, indicate that the agent has induced nephrotoxicity and/or the test compound or composition is effective in reducing the same. Expression levels can be determined, for example, at the protein and/or at the mRNA levels(s) by any suitable method.

The biological sample obtained can be, for example, a tissue sample (e.g., kidney biopsy in some embodiments), blood, or serum.

The following Examples provide illustrative embodiments of the invention. One of ordinary skill in the art will recognize the numerous modifications and variations that may be performed without altering the spirit or scope of the present invention. Such modifications and variations are encompassed within the scope of the invention. The Examples do not in any way limit the invention.

EXAMPLES

Materials and Methods

Part 1

The following materials and methods were used in Examples 1 and 2.

Experimental Groups

Rats were divided into six groups (n=6 in each) which included:
 (1) untreated control;
 (2) 2.5 mg/kg CsA;
 (3) 2.5 mg/kg CsA+2.5 mg/kg control antibody;
 (4) 2.5 mg/kg CsA+2.5 mg/kg anti-TGF-β antibody;
 (5) 2.5 mg/kg CsA+1.0 mg/kg anti-TGF-β antibody; and
 (6) isograft control.

Immunosuppression was accomplished by using CsA at a dosage of 2.5 mg/kg (intramuscularly) starting on the day of transplantation for the duration of the experiment. Anti-TGF-β antibody or control antibody was administered by intraperitoneal injection every third day until the time of sacrifice or organ rejection.

Preparation and Transplantation

Heterotopic heart transplants were performed on the entire study population as described in Hosenpud et al. (2000) Transplantation, 69:2173-2178. Donor rats were heparinized (1000 units, i.p.) and anesthetized with sodium pentobarbital (50 mg/kg, i.p.). An abdominal incision was made and extended from the thoracic cavity, and the chest wall was removed. Blunt dissection of the heart, aorta, and pulmonary artery was performed. The pulmonary veins and inferior vena cava were ligated, and the graft was excised and placed in iced physiologic saline. Recipient rats were then anesthetized with sodium pentobarbital (50 mg/kg, i.p.). A midline laparotomy was performed. The abdominal aorta and vena cava were dissected and clamped with straight vascular clamps to prevent bleeding. A longitudinal aortotomy and venotomy approximately 5 mm in length were performed. Using standard microvascular, techniques with 8-0 proline suture, end-to-side anastomoses of the aorta to the abdominal aorta and pulmonary artery to the inferior vena cava were made. Hemostasis was achieved, and the incision was closed with a 3-0 Vicryl™ suture.

Animal Monitoring, Sacrifice, Tissue Harvesting

Rats were monitored daily for evidence of allograft slowing and failure. They were then anesthetized with sodium pentobarbital (50 mg/kg, i.p.). Animals were exsanguinated via a native heart intraventricular puncture. Plasma samples were assayed for TGF-β protein using an ELISA kit (Promega, Madison, Wis.). Both kidneys were obtained (one for gene expression, one for histology and immunohistochemistry).

Immunosuppression Protocol

Immunosuppression was accomplished using CsA in the appropriate groups. CsA was used at a dosage of 2.5 mg/kg for the duration of the study with and without anti-TGF-β antibody (1D11) or control antibody. Treatment of anti-TGF-β antibody or control antibody was administered by intraperitoneal injection every third day until the time of sacrifice or organ rejection.

The control antibody (13C4) is also a murine monoclonal antibody (IgG1) that specifically binds shigella toxin. Both antibodies were produced and purified at Genzyme Corporation. Antibodies were determined to be free of detectable endotoxin.

Measurement of TGF-β Protein in Rat Plasma

TGF-β1 protein was measured as previously described (Khanna et al. (1999) Transplantation, 67:882-889). Plasma from rats was separated and stored at −70° C. TGF-β1 protein was assayed on acid activated samples by a sandwich ELISA using a commercial TGF-β1-specific kit (Promega, Madison, Wis.).

Histopathology and Immunohistochemistry for TGF-β1

One kidney from each animal was fixed in formalin and paraffin embedded. Hematoxylin and Eosin and Masson's trichrome staining was used to assess histologic changes. TGF-β was identified using standard immunohisto-chemical methods (Khanna et al. (1999) Transplantation, 67:882-889). Formalin-fixed, paraffin-embedded tissues were sectioned at 5 μm, deparaffinized in xylene and rehydrated in graded ethanol to PBS. After blocking endogenous peroxidase activity with methanol/peroxide (18:1 vol/vol) for 30 minutes, non-specific binding was blocked for 1 hour with 1.5% Avidin/Biotin diluted in PBS supplemented with 10% normal horse serum, and 3% BSA. The tissue sections were then incubated overnight at 4° C. with 1D11 mAb (50 mg/ml) in above-mentioned PBS; Following multiple washings with PBS, the slides were incubated for one hour with 1:1000 diluted biotin labeled anti-mouse IgG horse anti-serum at room temperature, again washed extensively in PBS and then in the ABC solution for 30 minutes. The slides were then developed for 10 minutes in diaminobenzidine (DAB) and rinsed with water for 10 minutes. The slides were then counterstained with hematoxylin followed by dehydration in graded ethanol and xylene. The slides were mounted with Permount™ for evaluation. Samples from each group were graded for histopathological changes and immunohistochemistry staining. The intensity of immunostaining was graded from 0 (no staining) to 4+ (maximum staining).

Detection of mRNA by Reverse Transcription and Polymerase Chain Reaction (PCR) in Kidney Tissues Total RNA was isolated from a small piece of kidney tissue from rats, using SV Total™ RNA isolation System (Promega Madison, USA), and quality of RNA was verified by 260/280-nm ratio. One microgram of RNA was reverse transcribed to cDNA using Superscript First Strand Synthesis™ system for RT-PCR (Life Technologies Rockville Md., USA). The amplification by polymerase chain reaction (PCR) was carried out using 1 μl of cDNA, and 2 μl each of 2.5 mM coding and non-coding oligonucleotide primers and Platinum PCR Supermix™ (Life Technologies, Rockville Md., USA). The primer sequences used and corresponding references as listed below.

```
1) TGF-β1 (Qian et al. (1990) Nucleic Acid Res., 18:3059)
coding:    ACG CCT GAG TGG CTG TCT TTT  (SEQ ID NO: 1)
noncoding: ACG TGG AGT TTG TTA TCT TTG  (SEQ ID NO: 2)

2) β-actin (Ponte et al. (1984) Nucleic Acids Res., 12:1687)
coding:    GAT CTG GCA CCA CAC CTT CTA  (SEQ ID NO: 3)
noncoding: GCA GGA TGG CGT GAG GGA GAG  (SEQ ID NO: 4)

3) collagen I (Frankel et al. (1988) DNA, 7:347-354)
coding:    CCC ACG TAG GTG TCC TAA AGT  (SEQ ID NO: 5)
noncoding: CCG TGG TGC TAA AAT AAT AAA  (SEQ ID NO: 6)

4) fibronectin (Schwarzbauer (1987) EMBO J., 6:2573-2580)
coding:    ATG ATG AGG TGC ACG TGT GT   (SEQ ID NO: 7)
noncoding: GAT GGG GTC ACA TTT CCA TC   (SEQ ID NO: 8)

5) MMP-2 (Pollock et al. (1995) J. Biol. Chem., 270:18786-18796)
coding:    GTG CTG AAG GAC ACA CTA AA   (SEQ ID NO: 9)
noncoding: TTG CCA TCC TTC TTT TCA AA   (SEQ ID NO: 10)

6) TIMP-2 (Battaglia et al. (1994) Exp. Cell Res., 213:398-403)
coding:    AAA CGA CAC TTA TGG CAA AC   (SEQ ID NO: 11)
noncoding: ACA GGA AGC GTC ACT TCT CT   (SEQ ID NO: 12)
```

For this semi-quantitative estimation of gene expression, cycle analysis was performed for each primer pair to determine the cycle number for optimal amplification. The PCR products were resolved in 1% agarose gel electrophoresis. Ethidium bromide stained specific bands were visualized under UV light and photographed. The densitometric analysis of the specific bands was made using Alpha-Imager™ (Alpha Innotech Corp., San Leandro, Calif., USA), and data are represented as the ratio of the specific gene to β-actin.

Data Analysis

Data reported is expressed as mean±SEM. Differences between appropriate groups were then analyzed using analysis of variance.

Example 1

Effect of Anti-TGF-β Antibody on Immunosuppressive Effects of CsA

The rat heterotopic heart transplant model employing the completely mismatched strain combination WF (RT1$^u$) into LEW (RT1$^1$), which was used in these studies, requires chronic immunosuppression to prevent rejection. TGF-β neutralizing antibody or an isotype matched control antibody were administered to determine whether TGF-β expression affects allograft survival in CsA-treated animals within the first 30 days.

Grafts from untreated animals rejected on average 11 days post-transplantation (n=6, 11±1.5). In contrast, grafts from CsA-treated animals survived for an average of 117 days (n=6, 117±9, p<0.001). To better understand the role of TGF-β in the pathogenesis of chronic rejection, heart transplant recipients were dosed with 1.0 or 2.5 mg/kg of anti-TGF-β antibody three times weekly beginning at three days post-transplantation. Control antibody was administered at identical concentration and dosing schedule. No statistically significant differences in survival were observed between untreated allografts and the group treated with CsA+2.5 mg/kg anti-TGF-β antibody, which had a mean survival time of 12.7±1.2 days (FIG. 1). CsA+2.5 mg/kg control antibody did not reject but were sacrificed on similar days as CsA+ anti-TGF-β antibody-treated animals for the sake of comparison of histological changes.

In sharp contrast, the animals that were injected with 1.0 mg/kg of antibody did not reject like animals that received CsA+2.5 mg/kg of anti-TGF-β antibody, and the mean survival time was 99±8 days. This was highly significant compared to the higher antibody group (p<0.01). The data at this time strongly supports the hypothesis that CsA's immunosuppressive effects are mediated by TGF-β, since anti-TGF-β at the concentration of 2.5 mg/kg totally abolished the efficacy of CsA. The current data demonstrates that rats injected with a lower dose of anti-TGF-β antibody had less severe renal pathological changes, presumably because the fibrogenic properties of TGF-β were neutralized by anti-TGF-β antibody.

Example 2

Effect of Anti-TGF-β Antibody on Nephrotoxic Effects of CsA

These experiments were performed to study the role of TGF-β in nephrotoxic effects of CsA. Along with CsA, recipients were also treated with TGF-β or control antibody (1.0 mg/kg) three times a week until the time of rejection. Groups included: untreated allografts; CsA treated allografts; CsA+Control antibody (1.0 mg/kg) treated allografts and CsA+anti-TGF-β antibody (1.0 mg/Kg), treated and isotype controls.

Renal Function

Renal function was measured by quantifying creatinine and blood urea nitrogen (BUN) levels in plasma of rats obtained after sacrifice from all experimental animals studied. Quantification was performed using kits from Sigma (St. Louis, USA). BUN levels were elevated in the CsA treated animals versus isograft controls (18.6±0.85 vs. 12.6±0.4 mg/dl; p<0.0001) and decreased levels were observed in CsA+anti-TGF-β antibody treated animals (13.8±0.63, p<0.03) but not with CsA+control treated animals (17.8±0.45). A significant increase in serum creatinine (0.75±0.03 vs. 0.43±0.2 mg/dl; p<0.0001) was observed in CsA treated recipients compared to isografts. Similarly to BUN levels, animals treated with CsA+anti-TGF-β antibody (0.49±0.06. p<0.003) but not control antibody (0.68±0.08) exhibited decreased creatinine levels.

Intrarenal Expression of TGF-β, Collagen, and Fibronectin mRNA

The results (FIG. 2) expressed as (gene/β-actin ratio, n=6 each) demonstrate the effect of long-term treatment of CsA with and without anti-TGF-β or control antibody on intrarenal mRNA expression of TGF-$β_1$, collagen and fibronectin.

TGF-β

Long-term treatment of CsA resulted in increased intrarenal expression of TGF-β mRNA (p<0.01) compared to isografts. There was no difference (p=0.12) in TGF-β mRNA expression between isografts and recipients treated with CsA anti-TGF-β antibody (1.0 mg/kg); whereas a significant difference (p<0.003) was observed between CsA and CsA+anti-TGF-β antibody (2.5 mg/kg) treated recipients. No difference was observed between CsA and CsA+control antibody treated recipients.

Collagen

Figure 2:
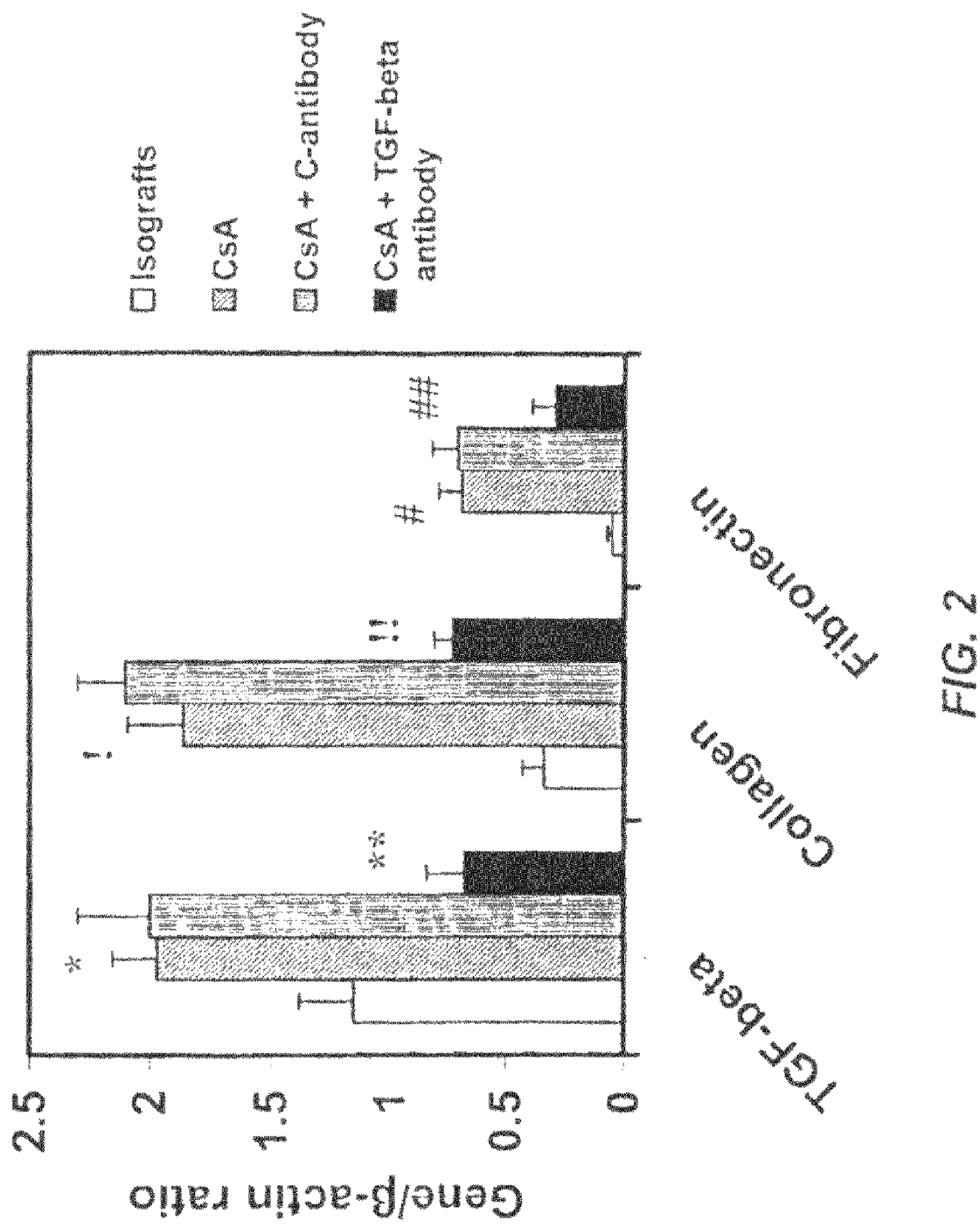
FIG. 2 shows the intrarenal expression levels of TGF-β, collagen, and fibronectin mRNA in various treatment groups described in FIG. 1. The results are expressed as a ratio of TGF-β, collagen or fibronectin to the housekeeping gene, β-actin. A statistically significant increase in expression of TGF-β, collagen, and fibronectin mRNA is seen in CsA treated recipients compared to isografts. A statistically significant decrease in expression of TGF-β, collagen, and fibronectin mRNA is seen in the CsA+anti-TGF-β antibody group as compared to CsA treated animals, whereas there is no difference with the CsA+control antibody group. (P values are as follows: TGF-β *p<0.02 and ** p<0.003; collagen ! p<0.0001 and !! p<0.008; fibronectin # p<0.0001 and ## p<0.002.)

Long-term treatment of CsA resulted in increased intrarenal expression of collagen mRNA (p<0.0001) compared to isografts. There was a significant difference (p<0.008) observed between CsA and CsA+anti-TGF-β antibody treated recipients (FIG. 2). No difference was observed between CsA and CsA+control antibody treated recipients.

Fibronectin

Similar results were obtained with fibronectin mRNA (FIG. 2), long-term treatment of CsA resulted in increased intrarenal, expression of fibronectin mRNA (p<0.0001) compared to isografts. A significant difference (p<0.002) was observed between CsA and CsA+anti-TGF-β antibody treated recipients. No difference was observed between CsA and CsA+control antibody treated recipients.

Intrarenal Expression of MMP-2 and TIMP-2

Figure 3:
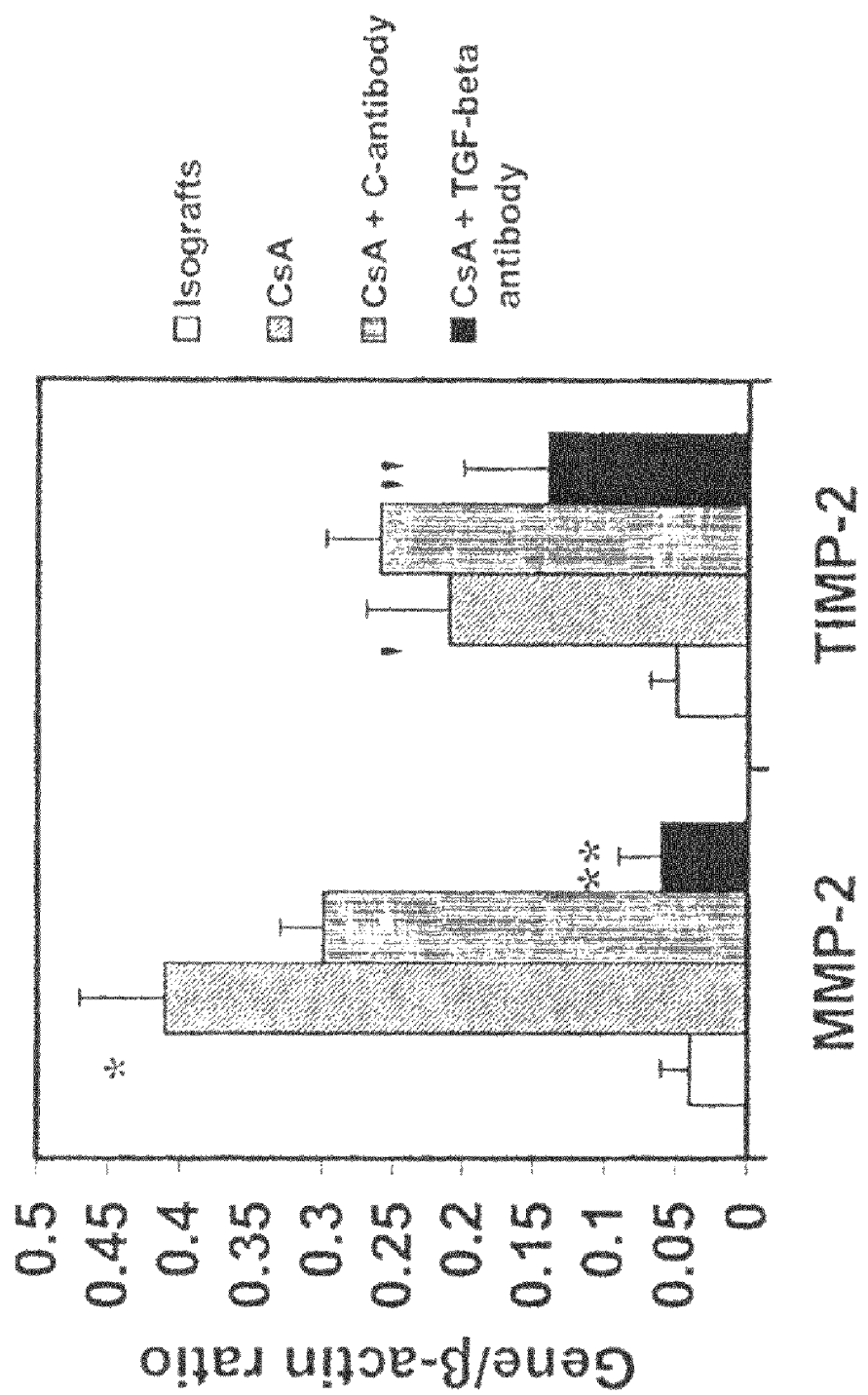
FIG. 3 shows intrarenal expression of MMP-2 and TIMP-2 mRNA. The results are expressed as a ratio of MMP-2 and TIMP-2 to the housekeeping gene, β-actin. A statistically significant increase in expression of MMP-2 and TIMP-2 is seen in CsA treated recipients as compared to isografts. A statistically significant decrease in expression of MMP-2 is seen in the CsA+anti-TGF-β antibody group as compared to CsA treated animals, whereas there is no difference with the CsA+control antibody group. For TIMP-2, a decrease in expression is seen in the CsA+anti-TGF-β antibody group as compared to CsA treated animals (albeit not statistically significant). (P values are as follows: MMP-2 *p<0.0002 and **p<0.004; TIMP-2! p<0.03 and !! p<0.18.)

The results demonstrate (FIG. 3) that long-term treatment of CsA resulted in increased intrarenal expression of MMP-2 mRNA (p<0.0002) compared to isografts. A significant difference (p<0.004) was observed between CsA and CsA+anti-TGF-β antibody treated recipients. No difference was observed between CsA and CsA+control antibody treated recipients. Anti-TGF-β antibody treated recipients demonstrated reduced, but not statistically different, intrarenal expression of TIMP-2 mRNA. No difference was observed between CsA and CsA+control antibody treated recipients.

Effect of A-TGF-β Antibody on Circulating Levels of TGF-β Protein

Figure 4:
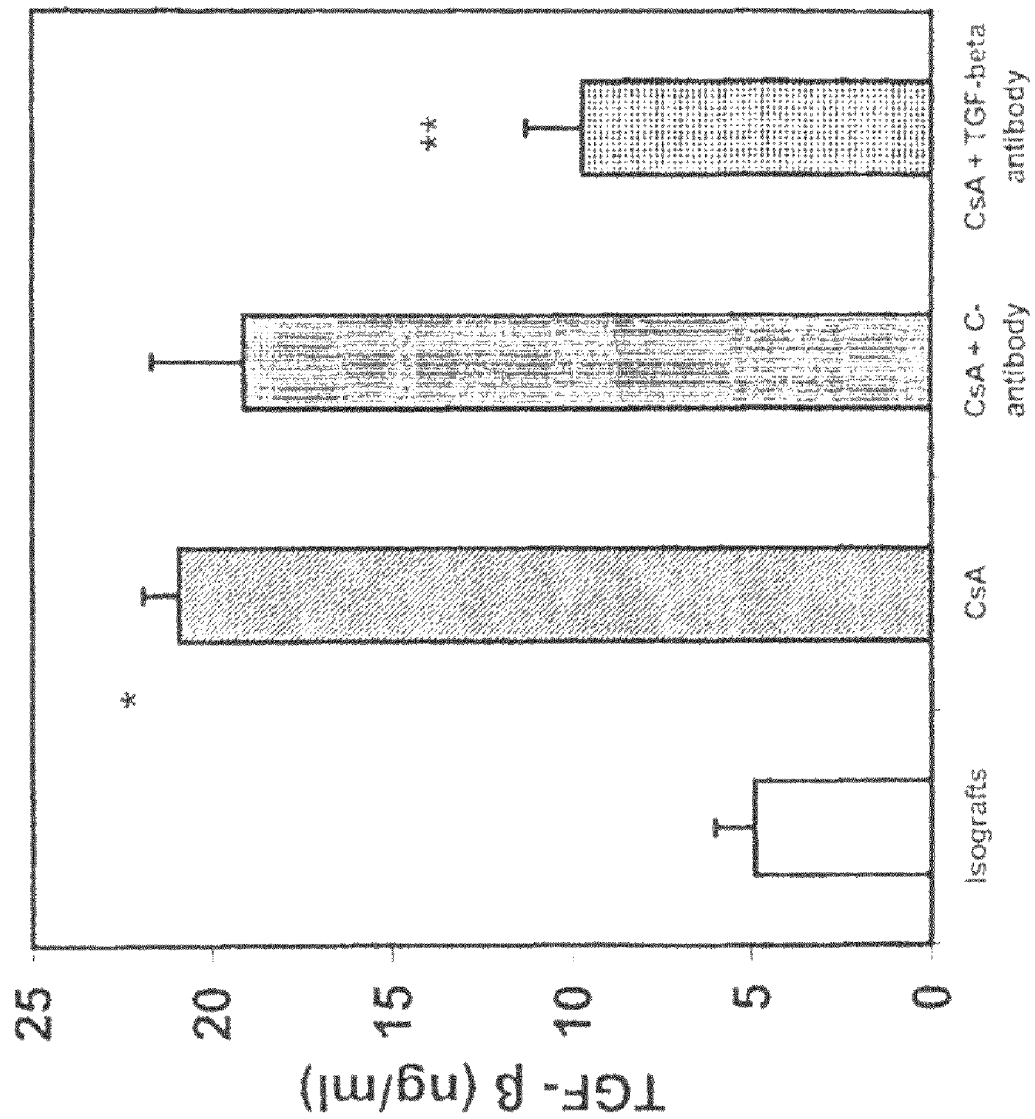
FIG. 4 shows plasma levels of TGF-β in animals treated with 1 mg/kg anti-TGF-β antibody as described in FIG. 1. A statistically significant Increase in plasma TGF-β levels is observed in animals treated with CsA as compared to isograft controls. A statistically significant decrease of TGF-β levels is seen in the CsA+anti-TGF-β antibody group as compared to CsA treated animals. (P values are as follows: *p<0.0001 and **p<0.003.)

These results (FIG. 4) demonstrate that compared to isografts, long-term treatment of CsA resulted in a significant ($p<0.0001$) increase in circulating levels of TGF-β protein. There was no difference in TGF-β levels among isografts and CsA+control antibody treated recipients; however, a statistically significant difference ($p<0.003$) was observed between CsA and CsA+anti-TGF-β antibody treated recipients.

Effect of Anti-TGF-β Antibody on Intrarenal Expression of TGF-β Protein

A significantly higher (3+–4+) staining of intrarenal TGF-β protein expression was observed in CsA-treated recipients, which was not different in the group treated with control antibody+CsA. TGF-β protein staining in animals treated with CsA+anti-TGF-β antibody (1.0 mg/kg) was reduced but remained slightly higher than isografts controls.

Effect of Anti-TGF-β Antibody on Renal Histology

Treatment with CsA resulted in histopathological changes akin to patients receiving long term treatment with CsA. Histopathological analysis of PAS and H&E stained slides from renal tissues of cardiac transplant recipient rats treated with 1) CsA alone; II) CsA+control antibody; and III) CsA+anti-TGF-β antibody (1.0 mg/kg) was performed. Tubular vacuolization and vascular changes, including increased PAS staining of vascular structures were found in CsA and CsA+control antibody treated animals. Although not all animals in group III had completely normal renal histology, the changes were only occasionally observed and were not prominent in this group. PAS staining was also diminished in anti-TGF-β treated recipients. The results demonstrate tubular and vascular changes including thickening of basement membrane and vacuolization in the CsA and CsA+control antibody treated animals.

Materials and Methods

Part 2

The following materials and methods were used in Examples 3-9.

Experimental Groups

Lewis (LEW RT1$^1$) rats were divided into the following five groups:
(1) untreated allograft control;
(2) untreated isograft control;
(3) TAC;
(4) TAC+anti-TGF-β antibody; and
(5) TAC+control antibody.

TAC was administered at 0.25 mg/kg i.m. for 90 days; and the anti-TGF-β antibody, 1D11, was administered at 1 mg/kg twice a week. The control antibody used was 13C4.

Rat Renal Transplantation

LEW RT1$^1$ or Wistar-Furth WF RT1$^u$ donor kidneys were transplanted into LEW RT1$^1$ recipients for isogeneic and allogeneic transplantation, respectively. (LEW RT1$^1$ and WF RT1$^u$) rats represent complete genetic disparity at both major and minor histocompatibility loci.)

The transplantation was performed as follows. A midline laparotomy was performed on renal donors following induction of general anesthesia with 50 mg/kg pentobarbital i.p. The left kidney was mobilized on its vascular pedicle and the ureter was divided. Following heparinization (1,000 U, i.p.), the left kidney was removed with a generous cuff of aorta and vena cava. The kidney was then flushed with iced saline and stored on ice until transplanted. In the recipients (anesthetized as described above), the infrarenal aorta and vena cava were exposed through a midline laparotomy. Using standard microvascular surgical techniques, the left donor kidney was anastomosed in an end-to-side fashion to the recipient vessels and the blood flow restored. The ureter was inserted through the bladder wall and stented with a short segment of PE50 tubing.

Animal Monitoring, Sacrifice, Tissue Harvesting

Rats housed in metabolic cages were monitored daily for evidence of graft rejection (i.e., a significant weight gain and decrease in urine output). Renal function was determined by changes in serum creatinine and BUN levels. At the time of rejection or at the completion of the observation period, animals were anesthetized with sodium pentobarbital (50 mg/kg i.p.). Following exsanguination via cardiac puncture, isografts and allografts were analyzed using routine histology, immunohistochemistry, Western blotting, and RT-PCR as described below.

BUN and Creatinine Levels

To assess renal function, serum BUN and creatinine were assayed using commercial kits from Wako Chemicals, Richmond, Va. and Oxford Biomedical Research, Oxford, Mich., respectively.

Allograft Histology, Immunohistochemistry and Quantification of Histopathological Changes A portion of transplanted kidneys from each animal was fixed with formalin and imbedded in paraffin. Hematoxylin and eosin (H&E) and periodic acid schiff (PAS) stainings were used to assess histological changes. Renal histological changes we quantified by standard procedures. The severity of the glomerular injury was scored as described in Khanna et al. (2000) Transplantation, 73:1543-1549. Briefly, in each field, at least 50-60 glomeruli were counted for each specimen and lesions were scored on a five-point scale (0, no proliferation, almost normal histology; 1, about 25% segmental lesion; 2, segmental lesion of greater than 25% but less than 50%; 3, fibrotic lesions with diffuse proliferation; 4, almost completely fibrotic changes). PAS staining was used to determine the extent of extracellular matrix protein accumulation (not scored). Interlobular arteries in H&E-stained slides and lesions were scored.

Plasma TGF-β Protein and Immunochemistry in Renal Tissues

Plasma levels of TGF-β protein were measured as described in Khanna et al. (1999) Transplantation, 67:882-889. Intrarenal protein expression of TGF-β was examined immunohistochemically as essentially as described in Khanna et al. (2000) Transplantation, 73:1543-1549; Khanna et al. (2002) Kidney Intl., 62:2257-63; and Khanna et al. (1999) Transplantation, 67:614-619. Formalin-fixed paraffin-embedded tissues were sliced into fine sections, deparaffinized in xylene and rehydrated in graded ethanol to phosphate-buffered saline (PBS). After blocking endogenous peroxidase activity for 30 minutes with methanol/$H_2O_2$ (18:1 vol/vol), nonspecific binding was blocked for 1 hour with 1.5% avidin/biotin diluted in PBS supplemented with 10% normal horse serum and 3% BSA. Tissue sections were incubated overnight at 4° C. with specific primary antibodies (50 µg/ml) in above-mentioned PBS. Following extensive washing in PBS, slides were incubated at room temperature for 1 hour with diluted (1:1,000) biotin-labeled anti-mouse IgG horse anti-serum and washed again extensively in PBS and then in the ABC solution for 30 minutes. The slides were developed for 10 minutes in diaminobenzidine (DAB) and rinsed in water for 10 minutes. The slides were then counterstained with hematoxylin and dehydrated in graded ethanol and xylene.

The slides were mounted with Permount™ for evaluation. Samples from each group were graded for histopathological changes and immunohistochemical staining. The intensity of immunostaining was graded from 0 (no staining) to 4+ (maximum staining). The severity of renal histology for each animal was blind-graded by two individuals for each of the following parameters: interstitial fibrosis, arterial changes, and glomerulosclerosis.

Detection of mRNA by Real-Time PCR

RT-PCR was performed using a Bio-Rad iCycler™ system (Bio-Rad, Hercules, Calif.). RNAs were isolated from renal tissues using a kit from Promega (Madison, N.J.) and reverse-transcribed into cDNAs by using a cDNA synthesis kit from Invitrogen (Carlsbad, Calif.). The specificity of primers was tested by running a regular PCR for 40 cycles at 95° C. for 20 seconds and 60° C. for 1 minute, followed by separating in ethidium bromide containing agarose gels. The real-time PCR was performed using a SYBR Supermix kit (Bio-RAD) (40 cycles at 95° C. for 20 s and 60° C. for 1 minute). The PCR efficiency was examined by serially diluting template cDNA. The melting curve data was collected to check the PCR specificity and proper negative controls were included in each assay. The mRNA level for each gene for each sample was normalized to $\beta$-actin mRNA and presented as 2-[(Ct/$\beta$-actin-Ct/gene of interest)] as described in Khanna et al. (2005) Nephron Exp. Nephrol., 101:119-126.

Western Blotting

Frozen tissues were homogenized in ice-cold PBS with 1% Triton X-100, 1 mM phenylmethysulfonyl fluoride, 35 ng/ml pepstatin A and 10 ng/ml leupeptin. After centrifugation, 50 µg: of protein was electrophoresed by SDS PAGE as described in Khanna et al. (2005) Nephron Exp. Nephrol., 101:119-126. Blots were probed with appropriate dilutions of a polyclonal anti-p22phox antibody (RS554, a gift from Marsh Lab, Bozeman, Mont.) or anti-NOX antibody (Santa Cruz Biotechnology, Santa Cruz, Calif.), incubated with a horseradish peroxidase-conjugated secondary antibody at a 1:5,000 dilution, and visualized by enhanced chemiluminescence.

Statistical Analysis

ANOVA and Student's t-test were used to assess differences between the group means for gene expression and plasma levels of TGF-$\beta$. The analysis was performed using a statistical software program from GraphPad, San Diego, Calif. Results were expressed as the mean±SEM, and two-tailed significance was determined at the level of p<0.05.

Example 3

Anti-TGF-$\beta$ Antibody Reduces the Effects of TAC on Kidney Function

Figure 5A:
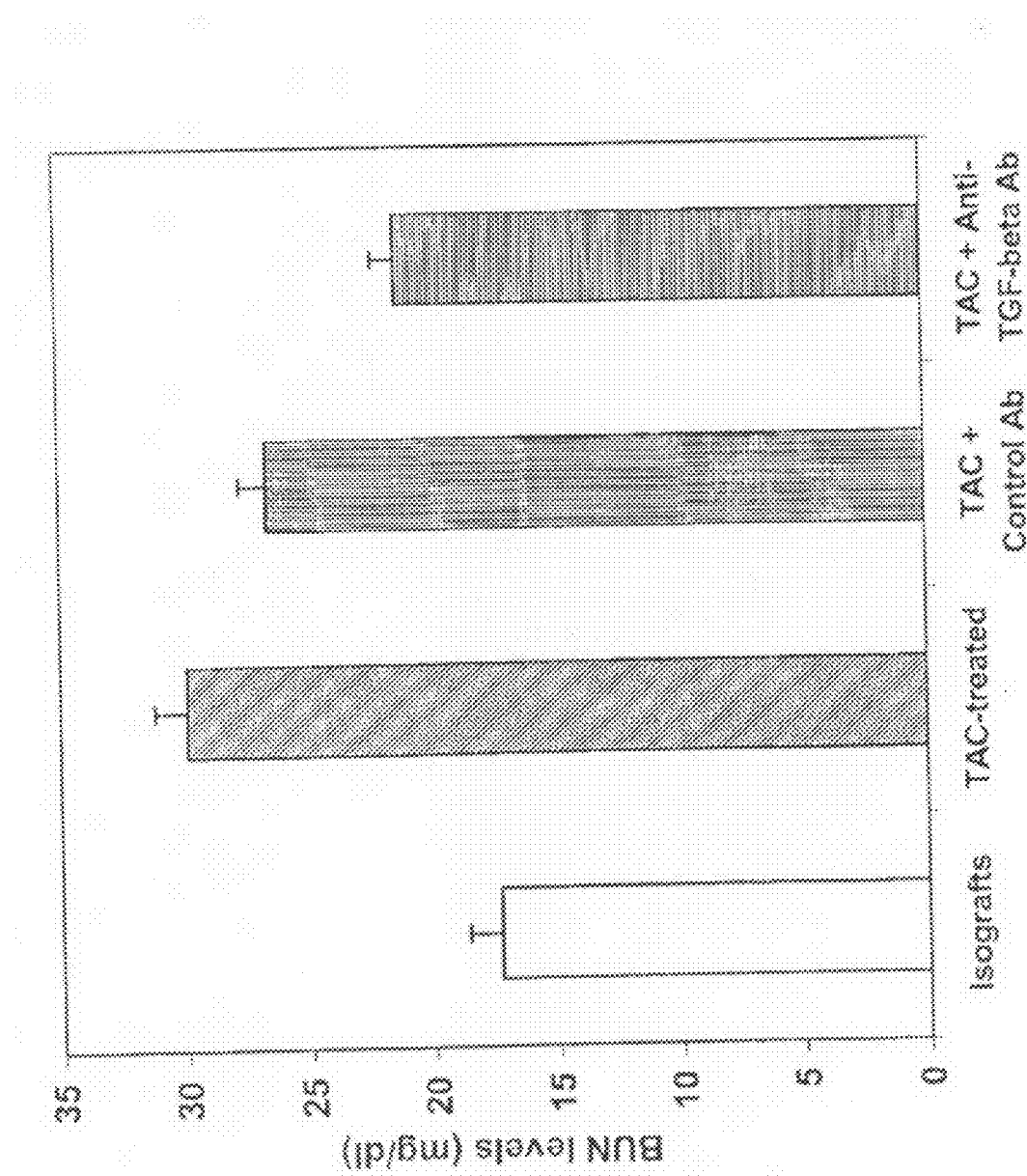
FIG. 5A shows BUN levels in animals treated with 0.25 mg/kg TAC for 90 days or in isograft controls. Along with TAC, recipients were also treated with anti-TGF-β or control antibody (1 mg/kg each) twice a week. Groups included: isografts, TAC-treated allografts, TAC+control antibody, and TAC+anti-TGF-β antibody. A statistically significant increase in BUN levels was observed in TAC-treated animals as compared to isograft controls (p<0.0001) or control antibody. Treatment with anti-TGF-β antibody decreased BUN levels (p<0.01) as compared to TAC alone. Treatment with control antibody also somewhat decreased BUN levels, but this decrease was not statistically significant.
Figure 5B:
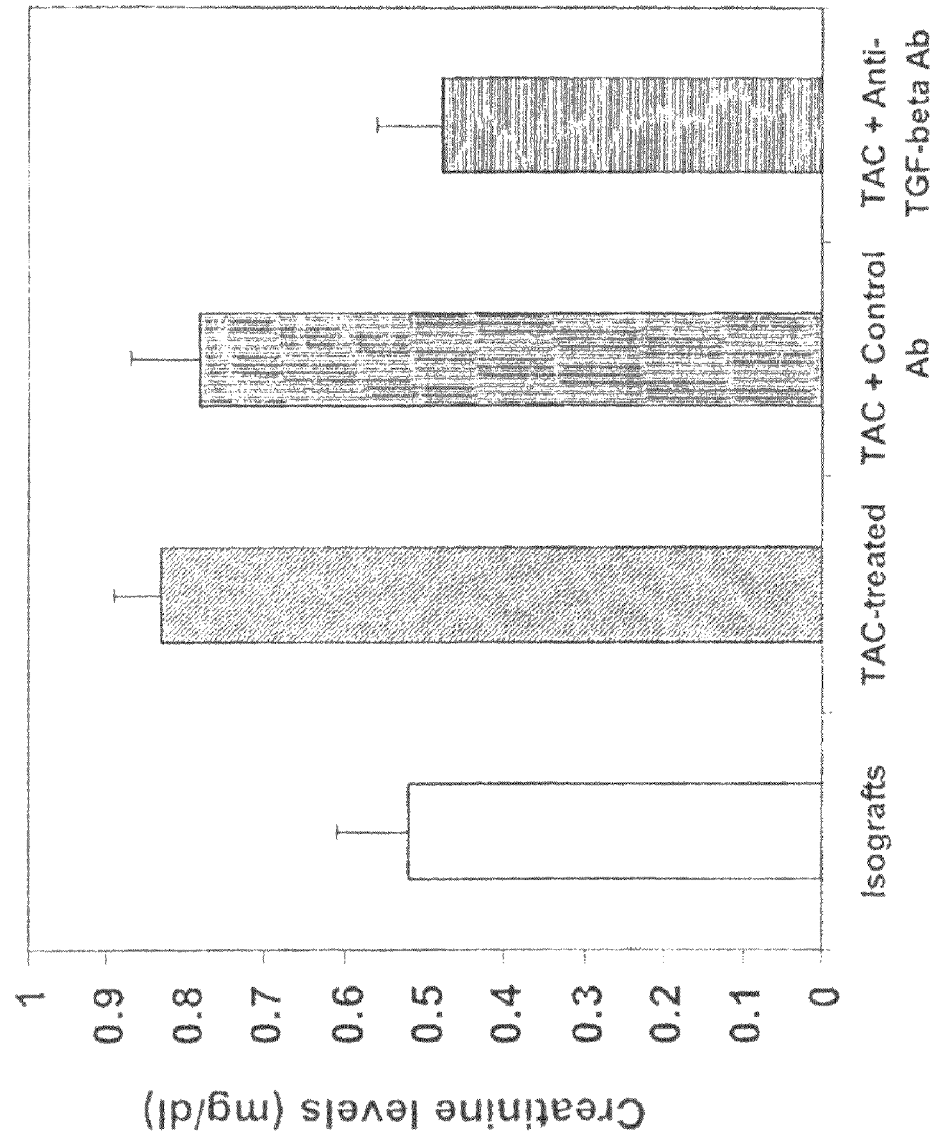
FIG. 5B shows creatinine levels in animals treated with TAC or in isograft controls. Animals were treated as described for FIG. 5A. A statistically significant increase in creatinine levels was observed in animals treated with TAC alone as compared to isograft controls (p<0.04) or control antibody. Treatment with anti-TGF-β antibody decreased BUN levels (p<0.02) as compared to TAC alone. Treatment with control antibody also somewhat decreased creatinine levels, but this decrease was not statistically significant.

BUN levels (FIG. 5A) were elevated in TAC-treated rats after 90 days of treatment versus isograft controls harvested at 90 days post transplantation (29.9±1.3 vs. 17.3±1.3 mg/dl; p<0.0001). Anti-TGF-$\beta$ antibody (21.3±0.9, p<0.01) but not control antibody (26.6±1.1 mg/dl) decreased BUN levels. Similarly, a significant increase in serum creatinine (0.83±0.06 vs. 0.52±0.09 mg/dl; p<0.04) was observed in TAC-treated recipients compared to time-matched isograft transplant controls. Similarly to BUN levels, anti-TGF-$\beta$ antibody (0.48±0.08 mg/dl; p<0.02) but not control antibody (0.78±0.09) inhibited TAC-induced creatinine levels (FIG. 5B).

Example 4

Figure 6:
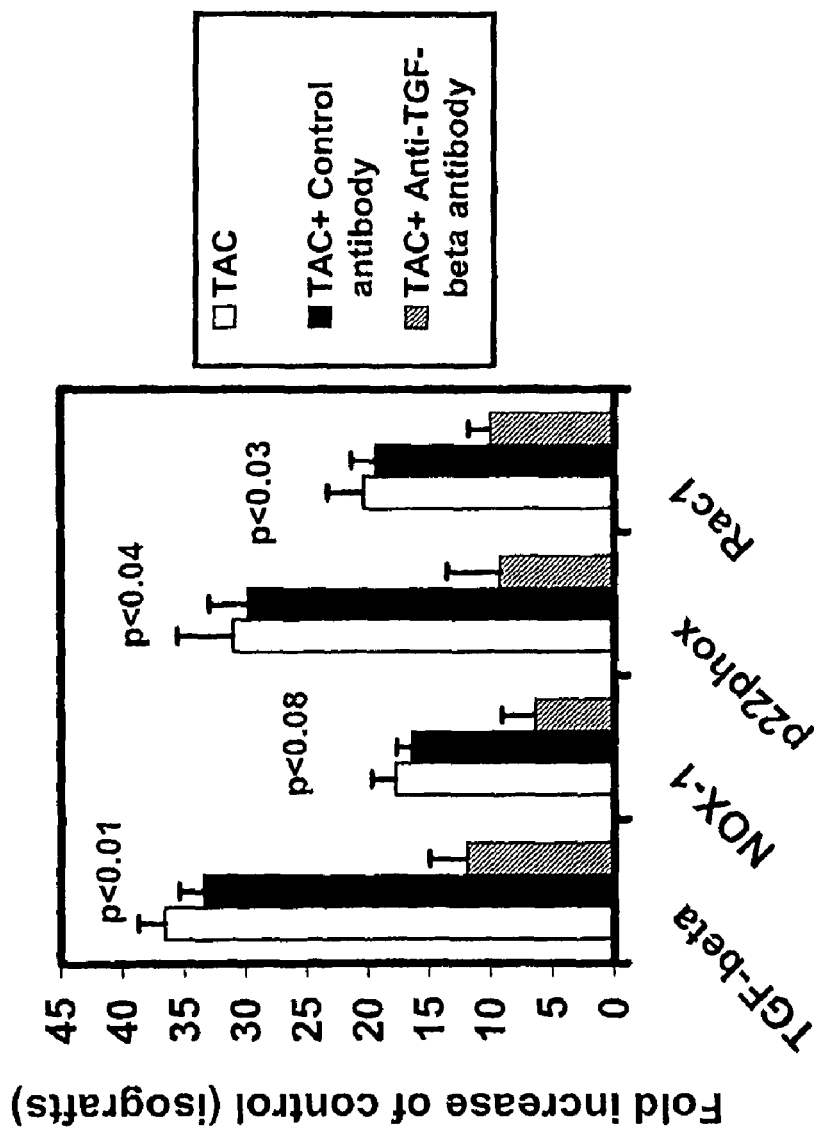
FIG. 6 shows the effect of anti-TGF-β antibody on intrarenal expression of TGF-β, NOX-1, $p22^{phox}$, and Rac-1 mRNA. Animals were treated as described for FIG. 5A. Anti-TGF-β antibody but not the control antibody inhibited TAC-induced intrarenal TGF-β, NOX-1, $p22^{phox}$, and Rac-1 mRNA expression.

Anti-TGF-$\beta$ Antibody and TAC-Induced Intrarenal Expression of TGF-$\beta$, NOX-1, p22$^{phox}$ and RAC-1 mRNA Intrarenal expression of TGF-$\beta$, NOX-1 and p22phox was analyzed by RT-PCR in renal tissues from (1) isografts, (2) TAC, (3) TAC+anti-TGF-$\beta$ antibody, and (3) TAC+control antibody treated animals at 90 days post transplantation. Treatment with TAC increased mRNA expression of TGF-$\beta$ (by 37-fold), NOX-1 (by 18-fold), and p22phox (by 31-fold), and RAC-1 (by 20-fold). Increases in gene expression were reduced by anti-TGF-$\beta$ antibody (p<0.01; p<0.008, p<0.04, and p<0.03, respectively) but were not by control antibody (FIG. 6). Results are presented with respect to isograft controls.

Example 5

Differential Intrarenal mRNA Expression of TGF-$\beta$, SOD and TRX

Figure 7:
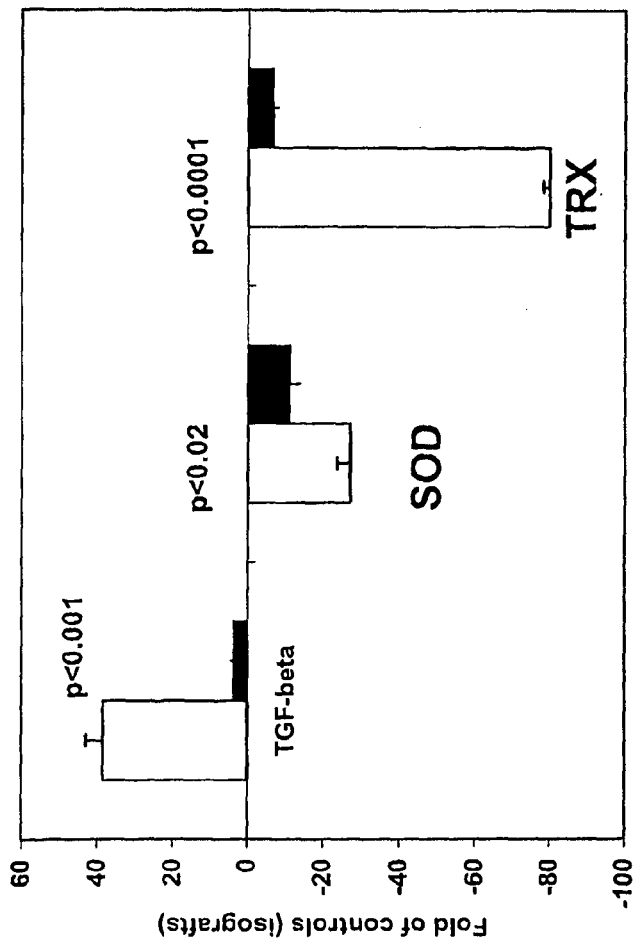
FIG. 7 shows the effect of TAC on TGF-β, SOD, and TRX mRNA expression in rat renal transplants. Animals were treated as described for FIG. 5A. TGF-β versus SOD and TRX mRNA were found to be reciprocally expressed in TAC-treated rat transplant recipients. Anti-TGF-β antibody inhibited intrarenal TGF-β but partially restored SOD and TRX mRNA expression.

To further examine the effect of prolonged treatment with TAC on antioxidant genes, intrarenal mRNA expression of SOD and TRX was determined. The data demonstrated that SOD and TRX mRNA decreased while TGF-$\beta$ mRNA increased in TAC-treated rats compared to isograft controls (FIG. 7). Treatment with TAC resulted in a 37-fold increase in TGF-$\beta$ mRNA whereas mRNA expression of SOD and TRX decreased 27- and 80-fold, respectively. SOD mRNA was partially reversed anti-TGF-$\beta$ antibody whereas TRX mRNA was completely reversed.

Example 6

Intragraft Expression of p22$^{phox}$ and NOX-1 Protein

Figure 8:
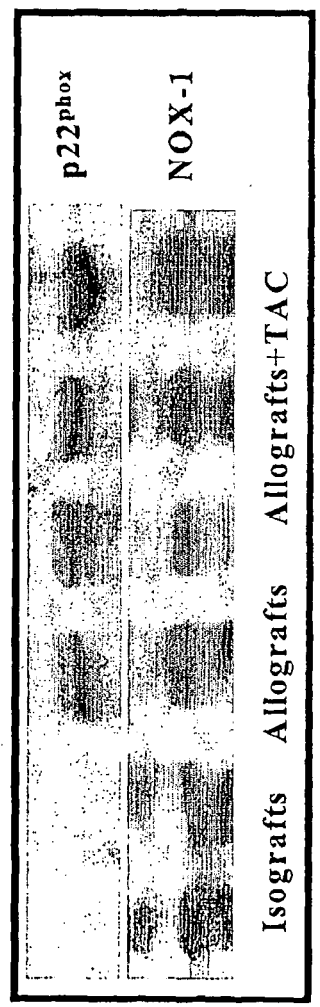
FIG. 8 shows the results of a Western blot analysis of $p22^{phox}$ and NOX-1 expression in animals treated as described for FIG. 5A. The intrarenal expression of $p22^{phox}$ and NOX-1 was elevated following treatment with TAC as compared to both, untreated allografts (last two lanes) and isograft controls (first two lanes).

Expression of p22$^{phox}$ and NOX-1 proteins was analyzed in kidney tissues from isografts, untreated allografts, and animals treated with TAC. Protein lysates (10 µg) were electrophoresed, transferred to nitrocellulose paper and probed with anti-p22$^{phox}$ and anti NOX-1 antibodies. As shown in FIG. 8, treatment with TAC resulted in increased intragraft expression of p22$^{phox}$ and NOX-1.

Example 7

Treatment with TAC Results in Nephrotoxicity Specific Histological Changes in the Renal Transplant The effect of TAC, TAC+a control antibody and TAC+anti-TGF-$\beta$ antibody treatment on morphological changes was assessed by histopathological examination in H&E- and PAS-stained thin kidney sections were evaluated.

The light microscopy findings of kidneys of control rats (isografts) showed normal glomeruli, afferent arterioles and tubule cells. In sharp contrast, the renal tissues of rats, which received TAC showed marked histological changes including, severe to moderate epical blebbing, hyalinization, glomerular basement thickening, a pattern of tubulointerstitial fibrosis and arteriolopathy of afferent arteriole and terminal portions of the interlobular arteries. These changes were not observed in co-administration of TAC and anti-TGF-β antibody. However, similar changes were seen in animals treated with TAC+control antibody. PAS-stained sections also show thickening of basement membrane compared to almost normal in the anti-TGF-β antibody treated recipients. The reversal of TAC-induced changes by anti-TGF-β antibody was observed. Histology in TAC+control antibody-treated animals was not different from that of TAC alone. Hyalinization and arteriolopathy tubulo-interstitial fibrosis and glomerular basement membrane thickening were observed in TAC and TAC+control antibody treated recipients but not in TAC+anti-TGF-β antibody treated recipients. Proximal tubular epithelial cell specific changes specific to renal toxicity were seen in TAC and TAC+control antibody treated rat transplant recipients and not in isografts or the TAC+anti-TGF-β antibody treated rats. A quantitative analysis demonstrated a statistically significant (p<0.036) difference in TAC-treated recipients compared to isografts which were not statistically different from TAC+anti-TGF-β antibody treated allografts.

Example 8

TAC Increases Intrarenal Expression of TGF-β

Immunohistochemistry was used to analyze the intrarenal expression of TGF-β protein in kidney tissues from recipients of renal transplants treated with TAC, TAC+anti-TGF-β antibody, TAC+control antibody-treated or untreated allografts. Renal sections were stained with anti-TGF-β antibody as described in Khanna et al. (2004) Circulation, 110:3822-3829. Besides hyalinization and arteriolopathy tubulo-interstitial fibrosis and glomerular basement membrane thickening, increased staining for TGF-β protein was observed in TAC and TAC+control antibody-treated recipients but was almost normal in TAC+anti-TGF-β antibody treated recipients (FIG. 8).

Example 9

Effect of TAC on Circulating Levels of TGF-β

Figure 9:
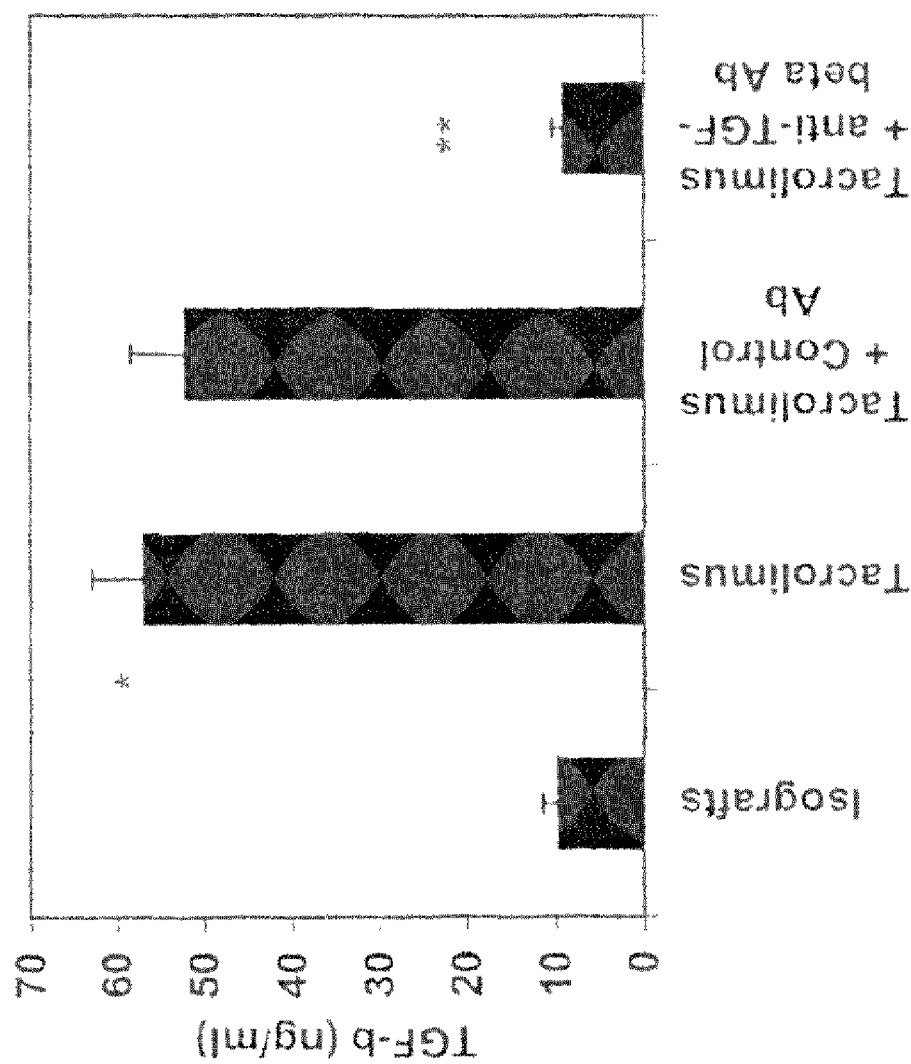
FIG. 9 shows the effect of TAC and/or anti-TGF-β antibodies on circulating levels of TGF-β protein in renal transplant recipients. Animals were treated as described for FIG. 5A. Circulating levels of TGF-β protein in plasma samples were quantified by ELISA. TAC-treated recipients exhibited a statistically significant increase of TGF-β expression as compared to isograft controls. A statistically significant decrease of TGF-β levels was observed in the TAC+anti-TGF-β antibody group as compared to TAC-treated animals; relative to treatment with TAC alone, no statistically significant difference in the TGF-β expression was observed as compared to TAC+control antibody-treated recipients. (P values are as follows: *p<0.01 and **p<0.01).

FIG. 9 demonstrates that long-term treatment with TAC resulted in a significant increase in circulating levels of TGF-β protein (9.8±1.7 vs. 57±6 ng/ml; p<0.01) as compared to isograft controls. There was no difference in TGF-β levels between isograft and TAC+control antibody treated recipients (57±6 vs. 52±6 ng/ml); however, a statistically significant difference (9±1.3 vs. 57±6 ng/ml; p<0.01) was observed between TAC and TAC+anti-TGF-β antibody treated recipients.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, patent applications, and biological sequences cited in this disclosure are incorporated by reference in their entirety. The citation of any references herein is not an admission that such references are prior art to the present invention.

Unless otherwise indicated, all numbers expressing quantities of ingredients, cell culture, treatment conditions, and so forth, used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating nephritis induced by an immunosuppressive agent in a mammal who is in need of immunosuppression and is treated with the immunosuppressive agent, wherein the immunosuppressive agent induces expression of TGF-β when administered to the mammal, the method comprising administering a TGF-β antagonist to the mammal in a therapeutically effective amount sufficient to alleviate the TGF-β-mediated nephrotoxic effects of the immunosuppressive agent without substantially interfering with the TGF-β-mediated immunosuppressive activity of the agent.

2. The method of claim 1, wherein the mammal is human.

3. The method of claim 1, wherein the immunosuppressive agent is selected from the group consisting of cyclosporine, tacrolimus, and sirolimus.

4. The method of claim 1, wherein the cyclosporine is cyclosporine A.

5. The method of claim 1, wherein the TGF-β antagonist is the antibody 1D11, deposited under ATCC Deposit Designation No. HB 9849 or a humanized derivative thereof.

6. The method of claim 1, wherein the mammal has an autoimmune disorder.

7. The method of claim 1, wherein the mammal has a transplant.

8. The method of claim 7, wherein the transplant is an allograft.

9. The method of claim 7, wherein the transplant is selected from the group consisting of heart, kidney, lung, liver, cornea, bone marrow, blood vessel and islet cell transplant.

10. The method of claim 1, wherein the TGF-β antagonist is administered at a dose at or below the dose equivalent to 2 mg/kg body weight of the 1D11 antibody when administered in rats.

11. The method of claim 1, wherein the TGF-β antagonist is administered at a dose equivalent to 1 mg/kg body weight of the 1D11 antibody when administered in rats.

12. The method of claim 5, wherein the antibody is a humanized derivative of 1D11.

13. The method of claim 5, wherein the antibody is a chimeric derivative of 1D11.

14. The method of claim 5, wherein the affinity constant of the humanized antibody is at least $10^8 M^{-1}$.

15. The method of claim 14, wherein the affinity constant is at least $10^9 M^{-1}$.

16. The method of claim 1, wherein the TGF-β antagonist is an anti-TGF-β antibody that specifically binds TGF-β1, TGF-β2, and TGF-β3.

17. The method of claim 16, wherein the affinity constant of the antibody is at least $10^6 M^{-1}$.

18. The method of claim 1, wherein the TGFβ antagonist is a human pan-specific anti-TGFβ antibody.

19. The method of claim 18, wherein the antibody is an IgG4 antibody with a variable heavy (VH) and variable light (VL) domain selected from the VH and VL airs of SEQ ID NOs: 13 and 14, or SEQ ID NOs: 15 and 16, or SEQ ID NOs: 17 and 18.

* * * * *

UNITED STATES PATENT AND TRADEMARK OFFICE
CERTIFICATE OF CORRECTION

PATENT NO. : 7,867,496 B2  Page 1 of 1
APPLICATION NO. : 11/663519
DATED : January 11, 2011
INVENTOR(S) : Ashwani K. Khanna and Steven Ledbetter It is certified that error appears in the above-identified patent and that said Letters Patent is hereby corrected as shown below:

Claim 18, column 34, lines 31 and 32, "TGFβ" should read -- TGF-β --.

Claim 19, column 34, line 35, "airs" should read -- pairs --.

Signed and Sealed this
Fifteenth Day of March, 2011

David J. Kappos
*Director of the United States Patent and Trademark Office*

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
acgcctgagt ggctgtcttt t                                              21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
acgtggagtt tgttatcttt g                                              21
```

```
<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
gatctggcac cacaccttct a                                              21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gcaggatggc gtgagggaga g                                              21

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
cccacgtagg tgtcctaaag t                                              21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ccgtggtgct aaaataataa a                                              21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
atgatgaggt gcacgtgtgt                                                20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gatggggtca catttccatc                                                20

<210> SEQ ID NO 9
<211> LENGTH: 20
<212> TYPE: DNA
<213> ORGANISM: Artificial Sequence
<220> FEATURE:
```

<223> OTHER INFORMATION: Primer

<400> SEQUENCE: 9
gtgctgaagg acacactaaa                                                    20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ttgccatcct tcttttcaaa                                                    20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
aaacgacact tatggcaaac                                                    20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
acaggaagcg tcacttctct                                                    20

<210> SEQ ID NO 13
<211> LENGTH: 120
<212> TYPE: PRT
<213> ORGANISM: Artificial sequence
<220> FEATURE:
<223> OTHER INFORMATION: Synthetic sequence

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser
        115                 120

<210> SEQ ID NO 14
<211> LENGTH: 108

```
<212> TYPE: PRT
<213> ORGANISM: Artificial sequence
<220> FEATURE:
<223> OTHER INFORMATION: Synthetic sequence

<400> SEQUENCE: 14

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
            100                 105

<210> SEQ ID NO 15
<211> LENGTH: 120
<212> TYPE: PRT
<213> ORGANISM: Artificial sequence
<220> FEATURE:
<223> OTHER INFORMATION: Synthetic sequence: Amino acid sequence of
      PET1074B9 VH

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Leu Pro Arg Ala Phe Val Leu Asp Ala Met Asp Tyr Trp Gly Gln
            100                 105                 110

Gly Thr Leu Val Thr Val Ser Ser
        115                 120

<210> SEQ ID NO 16
<211> LENGTH: 108
<212> TYPE: PRT
<213> ORGANISM: Artificial sequence
<220> FEATURE:
<223> OTHER INFORMATION: Synthetic sequence: Amino acid sequence of
      PET1074B9 VL

<400> SEQUENCE: 16

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30
```

```
Tyr Leu Ala Trp Tyr Gln Gln Lys Pro Gly Gln Ala Pro Arg Leu Leu
            35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
            100                 105

<210> SEQ ID NO 17
<211> LENGTH: 121
<212> TYPE: PRT
<213> ORGANISM: Artificial sequence
<220> FEATURE:
<223> OTHER INFORMATION: Synthetic sequence: Amino acid sequence of
      PET1287A10 VH

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Ser
            20                  25                  30

Phe Ile Asn Trp Val Arg Gln Ala Pro Gly Gln Gly Leu Glu Trp Met
            35                  40                  45

Gly Gly Ile Ile Pro Ile Phe Asp Ile Thr Asn Tyr Ala Gln Lys Phe
    50                  55                  60

Gln Ser Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Gly Asn Tyr Ala Leu Asp Ala Met Asp Tyr Trp Gly
            100                 105                 110

Gln Gly Thr Leu Val Thr Val Ser Ser
        115                 120

<210> SEQ ID NO 18
<211> LENGTH: 108
<212> TYPE: PRT
<213> ORGANISM: Artificial sequence
<220> FEATURE:
<223> OTHER INFORMATION: Synthetic sequence: Amino acid sequence of
      PET1287A10 VL

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Phe Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Tyr Asp Ser Pro
                85                  90                  95
Ile Thr Phe Gly Gln Gly Thr Arg Leu Glu Ile Lys
                100             105
```